(12) United States Patent
Lacaze et al.

(10) Patent No.: US 12,233,179 B2
(45) Date of Patent: Feb. 25, 2025

(54) SYSTEMS AND METHODS FOR AUTONOMOUS STERILIZATION

(71) Applicant: Robotic Research, LLC, Clarksburg, MD (US)

(72) Inventors: Alberto Daniel Lacaze, Potomac, MD (US); Joseph Putney, Waterford, VA (US); William Becker, Gaithersburg, MD (US); Steve Rotundo, Gaithersburg, MD (US); Karl Nicholas Murphy, Cocoa Beach, FL (US)

(73) Assignee: Robotic Research OpCo, LLC, Clarksburg, MD (US)

( * ) Notice: Subject to any disclaimer, the term of this patent is extended or adjusted under 35 U.S.C. 154(b) by 934 days.

(21) Appl. No.: 17/231,967

(22) Filed: Apr. 15, 2021

(65) Prior Publication Data

US 2021/0322613 A1  Oct. 21, 2021

Related U.S. Application Data

(60) Provisional application No. 63/010,475, filed on Apr. 15, 2020, provisional application No. 63/011,040, filed on Apr. 16, 2020, provisional application No. 63/019,455, filed on May 4, 2020.

(51) Int. Cl.
| | | |
|---|---|---|
| A61L 2/00 | (2006.01) | |
| A61L 2/24 | (2006.01) | |
| A61L 9/00 | (2006.01) | |
| A62B 7/08 | (2006.01) | |
| G01N 21/00 | (2006.01) | |
| G05B 9/00 | (2006.01) | |
| G06N 20/00 | (2019.01) | |

(52) U.S. Cl.
CPC ............... *A61L 2/24* (2013.01); *G06N 20/00* (2019.01); *A61L 2202/14* (2013.01)

(58) Field of Classification Search
CPC .... A61L 2/24; A61L 2202/14; A61L 2202/25; A61L 2209/212
USPC ...... 422/24, 28, 62, 112, 119, 123, 305–306
See application file for complete search history.

(56) References Cited

U.S. PATENT DOCUMENTS

2012/0223216 A1* 9/2012 Flaherty ............... G05D 1/0242
901/1

* cited by examiner

*Primary Examiner* — Monzer R Chorbaji
(74) *Attorney, Agent, or Firm* — RowanTree Law Group, PLLC; Carson C. K. Fincham

(57) ABSTRACT

Systems and methods for autonomous sterilization of vehicles includes coded logic or processing instructions to determine (i) when sterilization should occur (or not occur), (ii) where sterilization should occur (or not occur), and/or (iii) how sterilization should occur (e.g., which method to use, how long to conduct, and/or which parameter values/settings to employ). The sterilization system may autonomously determine when it is safe to sterilize an environment/location and/or how such sterilization should be carried out. Autonomous sterilization systems and/or processes described herein may permit facilities and/or services to remain open and/or available at higher rates than current offline processes permit, thereby increasing availability.

20 Claims, 10 Drawing Sheets

SYSTEMS AND METHODS FOR AUTONOMOUS STERILIZATION

CROSS-REFERENCE TO RELATED APPLICATIONS

This application claims benefit and priority under 35 U.S.C. § 119(e) to, and is a Non-provisional of, (i) U.S. Provisional Patent Application No. 63/010,475 filed on Apr. 15, 2020 and titled "Self-Sanitizing Vehicle", (ii) U.S. Provisional Patent Application No. 63/011,040 filed on Apr. 16, 2020 and titled "Safe UV Sanitizer", and (iii) U.S. Provisional Patent Application No. 63/019,455 filed on May 4, 2020 and titled "Safe UV Sanitizer Vehicle", each of which is hereby incorporated by reference herein in its entirety.

BACKGROUND

The COVID-19 pandemic has brought the need for effective sanitation and sterilization to the forefront. It has also highlighted many shortcomings of current sterilization practices. There are two primary sterilization methods for surfaces, for example, namely the use of chemical sterilization formulations and the use of Ultra Violet (UV) light (or radiation). While some sterilization chemicals are available over-the-counter and can be applied with little concern for human exposure (e.g., Lysol® brand products), stronger (and thus more effective) chemicals and UV radiation can pose serious health risks to humans. Accordingly, such stronger sterilization methods are currently employed in offline sterilization processes. Hospitals and doctors sterilize instruments and treatment areas between uses (typically overnight), for example, and the pandemic has seen many public establishments (including school buildings) institute shorter business hours available to the public so that strong and thorough sterilization procedures may be implemented between openings (e.g., again, typically overnight).

BRIEF DESCRIPTION OF THE DRAWINGS

An understanding of embodiments described herein and many of the attendant advantages thereof may be readily obtained by reference to the following detailed description when considered with the accompanying drawings, wherein.

DETAILED DESCRIPTION

I. Introduction

Figure 1:
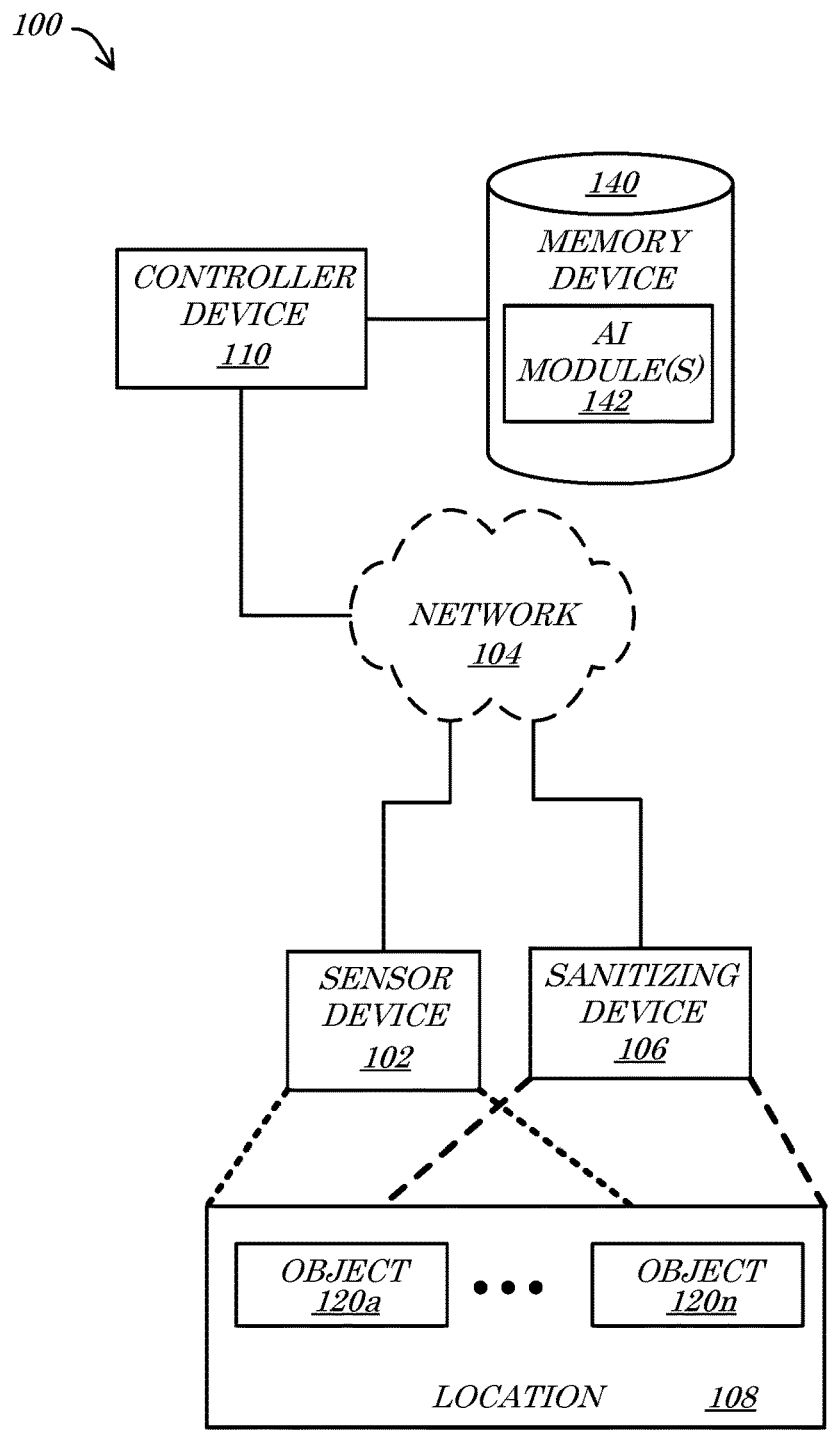
FIG. 1 is a block diagram of a safe sterilization system according to some embodiments.

Embodiments of the present invention provide systems and methods for autonomous sterilization that overcome various deficiencies and/or shortcomings of current and prior sterilization systems and methods. Typical overnight sterilization procedures are effective, for example, but cause significant down-time for the affected institution, object, and/or entity. Such procedures also provide contact tracing benefits by separating one day from the next, but are incapable of addressing sterilization needs during any given day. Further, because of the long time lag (twenty-four hours (24-hrs)) between sterilization, such procedures are not effective at increasing proactive protection (e.g., only the first few riders of a public transit system the morning it opens after a deep clean may be protected by being in a sterile environment, while all riders thereafter must be exposed to an environment tainted by the first group of riders, with the potential contamination levels escalating throughout the day).

According to some embodiments, logic (e.g., Artificial Intelligence (AI) logic) may be utilized to determine (i) when sterilization should occur (or not occur), (ii) where sterilization should occur (or not occur), and/or (iii) how sterilization should occur (e.g., which method to use, how long to conduct, and/or which parameter values/settings to employ). In some embodiments, for example, an AI-based sterilization system may autonomously determine when it is safe to sterilize an environment/location and/or how such sterilization should be carried out. According to some embodiments, autonomous sterilization systems and/or processes described herein may permit facilities and/or services to remain open and/or available at higher rates than current offline processes permit, thereby increasing availability. With respect to many industries and/or services such as public transportation systems and schools, increased uptime may decrease costs and increase service levels provided to the public/students.

In some embodiments, the ability to safely and efficiently conduct sterilization processes without removing a structure and/or vehicle from service (e.g., piece-meal and/or stage-timing sterilization) may also or alternatively increase public protection by increasing the granularity of contact tracing time slices (e.g., decreasing the time period between sterilization activities). More frequent sterilization processes that are able to be conducted during uptime and/or during shorter-duration downtime intervals, for example, may result in lower exposure probabilities to those making use of the provided products and/or services.

According to some embodiments, autonomous sterilization systems may comprise one or more sensors disposed to identify and/or detect a human (and/or other animal or object) that requires protection from sterilization processes, one or more selectively activated sterilization devices, and/or a controller device operable to execute stored instructions (such as AI logic) to selectively activate the one or more sterilization devices based on the identification/detection (or lack thereof) of the human/animal/object.

II. Autonomous Sterilization Systems

Referring initially to FIG. 1, a block diagram of a safe sterilization system 100 according to some embodiments is shown. In some embodiments, the system 100 may comprise a sensor device 102 in communication with a network 104. According to some embodiments, the system 100 may comprise a sanitizing device 106 in communication with the network 104. In some embodiments, the sensor device 102 and/or the sanitizing device 106 may be disposed in proximity to or in a particular location 108. The sensor 102 may be disposed (e.g., coupled, mounted, orientated) to sense and/or detect data descriptive of the location 108, and/or the sanitizing device 106 may be disposed (e.g., coupled, mounted, orientated) to sanitize (e.g., sterilize) at least a portion of the location 108. According to some embodiments, the sensor device 102 and/or the sanitizing device 106 may be in communication with (e.g., via the network 104) a controller device 110, e.g., that selectively activates and/or communications with either or both of the sensor device 102 and the sanitizing device 106. In some embodiments, such as in the case that the controller device 110 is disposed in proximity to the sensor device 102 and/or the sanitizing device 106 (e.g., in proximity to, at, or in the location 108), the network 104 may not be required or may comprise only a localized network such as a set of Printed Circuit Board (PCB) traces, discrete wires and/or cables, and/or a computerized bus.

In some embodiments, the controller device 110 may be operable to receive data from the sensor device 102 and, based at least in part on the received data, trigger the sanitizing device 106 to sanitize one or more portions of the location 108. According to some embodiments, one or more objects 120*a-n* may be disposed and/or detected (e.g., by the sensor 102) at the location 108. The one or more objects 120*a-n* may comprise targets for sterilization, for example, and/or may comprise areas and/or items that are to be avoided (e.g., prone to damage from sterilization). In some embodiments, any or all of the devices 102, 106, 110 may comprise and/or be in communication with a data storage and/or memory device 140. The memory device 140 may store, for example, one or more AI modules 142 (e.g., sets of logic, rules, and/or thresholds) that, when executed by the controller device 110 cause the selective activation and/or control of the sensor device 102 and the sanitizing device 106.

According to some embodiments, as depicted in FIG. 1, any or all of the devices 102, 106, 110, 140 (or any combinations thereof) may be in communication via the network 104. In some embodiments, communications between and/or within the devices 102, 106, 110, 140 of the system 100 may be utilized to capture and analyze images and/or other readings or input from the sensor device 102 with respect to (and/or descriptive of) the location 108 (and/or the objects 120*a-n* thereof). The controller device 110 may identify, detect, and/or derive an indication of an existence and/or location of one or more of the objects 120*a-n* at the location 108, based on input received from the sensor device 102, for example, by execution of the AI module 142 stored in the memory device 140. According to some embodiments, such indication may be calculated, looked up, derived, defined, computed, and/or otherwise determined by analysis of imagery or other data captured by the sensor device 102 pursuant to an execution of AI module 142 defined by the controller device 110.

Fewer or more components 102, 104, 106, 108, 110, 120*a-n*, 140, 142 and/or various configurations of the depicted components 102, 104, 106, 108, 110, 120*a-n*, 140, 142 may be included in the system 100 without deviating from the scope of embodiments described herein. In some embodiments, the components 102, 104, 106, 108, 110, 120*a-n*, 140, 142 may be similar in configuration and/or functionality to similarly named and/or numbered components as described herein. In some embodiments, the system 100 (and/or portion thereof) may comprise an AI-based autonomous sanitization and/or sterilizing system and/or platform programmed and/or otherwise configured to execute, conduct, and/or facilitate the methods 500, 600 of FIG. 5 and/or FIG. 6 herein, and/or portions or combinations thereof.

According to some embodiments, the sensor device 102, may comprise any type, quantity, and/or configuration of data gathering and/or input device that is or becomes known or practicable. According to some embodiments, the sensor device 102 may comprise one or more sensors configured and/or coupled to sense, measure, calculate, and/or otherwise process or determine data descriptive of the location 108 and/or the objects 120*a-n*, and/or the environment in which they are disposed, such as photographic data, video data, light measurements, strain measurements, temperature readings, moisture and/or humidity readings, sound readings, vibration readings, weight readings, Infrared Radiation (IR) and/or microwave readings (e.g., motion sensor readings and/or IR intensity readings), and/or location readings. In some embodiments, the sensor device 102 may be disposed and/or positioned to acquire data descriptive of the location 108, the objects 120*a-n*, and/or the environment(s) thereof, but may be part of a separate device and/or object. The sensor device 102 may comprise, for example, a camera and/or other sensor coupled and/or mounted to capture data descriptive of the location 108 (e.g., the presence and/or location(s) of the objects 120*a-n*). In some embodiments, sensor data may be provided to the AI module 142 and/or the controller device 110 to identify movements of the objects 120*a-n* at the location 108 (e.g., entry of objects 120*a-n* into the location 108, positions of the objects 120*a-n* within the location 108, and/or departure of the objects 120*a-n* from the location 108). According to some embodiments, the sensor device 102 may comprise one or more of a Light Detection and Ranging (LiDAR), Infrared Radiation (IR), Passive IR (PIR), radar, camera, stereo camera, 3D-camera, ultrasonic, acoustic, pressure, weight, temperature, bacterial, virus, and/or other sensor device and/or combinations thereof.

In some embodiments, the network 104 may comprise a Local Area Network (LAN; wireless and/or wired), cellular telephone, Bluetooth®, Near Field Communication (NFC), and/or Radio Frequency (RF) network with communication links between the controller device 110, the sensor 102, the sanitizing device 108, the objects 120*a-n*, and/or the memory device 140. In some embodiments, the network 104 may comprise direct communication links between any or all of the components 102, 106, 110, 120*a-n*, 140 of the system 100. The sensor device 102 may, for example, be directly interfaced or connected to one or more of the controller device 110 and/or the sanitizing device 108 via one or more wires, cables, wireless links, and/or other network components, such network components (e.g., communication links) comprising portions of the network 104. In some embodiments, the network 104 may comprise one or many other links or network components other than those depicted in FIG. 1. The controller device 110 may, for example, be connected to the memory device 140 via various cell towers, routers, repeaters, ports, switches, and/or other network components that comprise the Internet and/or a cellular telephone (and/or Public Switched Telephone Network (PSTN)) network, and which comprise portions of the network 104.

While the network 104 is depicted in FIG. 1 as a single object, the network 104 may comprise any number, type, and/or configuration of networks that is or becomes known or practicable. According to some embodiments, the network 104 may comprise a conglomeration of different sub-networks and/or network components interconnected, directly or indirectly, by the components 102, 106, 110, 120*a-n*, 140 of the system 100. The network 104 may comprise one or more cellular telephone networks with communication links between the sanitizing device 108 and the controller device 110, for example, and/or may comprise an NFC or other short-range wireless communication path, with communication links between the sensor device 102, the sanitizing device 108, and/or one or more of the objects 120*a-n*, for example.

According to some embodiments, the sanitizing device 106 may comprise any type, quantity, and/or configuration of cleaning, sterilizing, and/or sanitizing device or substance that is or becomes known or practicable. The sanitizing device 106 may comprise, for example, a chemical cleaning substance dispenser, atomizer, vaporizer, sprayer, hose, nozzle, and/or other chemical substance (e.g., gas, liquid, solid, and/or semi-solid/gel) emitter or delivery system device, such as one or more OW-DH-1600 large capacity stand-alone misters available from Oil Works & Company, LLC of Venice, FL. In some embodiments, the sanitizing device 106 may comprise one or more UV radiation emitters that is operable to emit UV-A (e.g., "blacklight"), UV-B, and/or UV-C wavelengths of light, such as a Blue-Tube UV™ TUV-BTST2 device available from the Fresh-Aire UV® of the DiversiTech® Corporation of Buford, GA According to some embodiment, whether chemical sterilization or UV sterilization is utilized, the sanitizing device 106 may comprise one or more directional and/or steerable nozzles, ports, shields, and/or other location-directional apparatus operable to direct the emitted sanitizing substance (chemical, light, etc.) in or more particular directions, patterns, etc.

In some embodiments, the location 108 may comprise any type, quantity, and/or configuration of location(s) that is or becomes known or practicable. The location 108 may comprise a fixed location such as a school, store, bus stop, street corner, cubicle, seating area, and/or passageway (e.g., hallway, doorway, window, etc.), for example, or may comprise a mobile location and/or object such as a vehicle. The location 108 may comprise, in some embodiments, a cargo and/or passenger vehicle, mass transit vehicle, and/or fleet vehicle (e.g., a car, truck, train, boat, ship, bus, and/or airplane), for example, that is utilized to transport or move one or more of the objects 120*a-n* (e.g., cargo, passengers, etc.). In some embodiments, the location 108 may comprise a combination of mobile and fixed locations such as a bus stop at which a bus is stopped to pickup and/or discharge passengers. In some embodiments, such as in the case that the location 108 comprises a vehicle, the vehicle may comprise an autonomous vehicle such as an autonomous bus, e.g., the Olli™ self-driving shuttle available from Local Motors™ of Phoenix, AZ.

According to some embodiments, the controller device 110 may comprise an electronic and/or computerized controller device, such as a computer server communicatively coupled to interface with the sensor device 102 and/or the sanitizing device 106 (directly and/or indirectly). The controller device 110 may, for example, comprise one or more PowerEdge™ R830 rack servers manufactured by Dell®, Inc. of Round Rock, TX which may include one or more Twelve-Core Intel® Xeon® E5-4640 v4 electronic processing devices. In some embodiments, the controller device 110 may comprise a plurality of processing devices specially programmed to execute and/or conduct processes that are not practicable without the aid of the controller device 110. The controller device 110 may, for example, execute one or more coded rules (e.g., the AI module(s) 142) to manage wireless communications with the sensor device 102 and/or the sanitizing device 106, and/or may provide complex AI-based image/object analysis services and/or analysis, either of which may not be capable of being conducted without the benefit of the specially-programmed controller device 110. According to some embodiments, the controller device 110 may be located remotely from one or more of the sensor device 102, the sanitizing device 106, and/or the location 108. The controller device 110 may also or alternatively comprise a plurality of electronic processing devices located at one or more various sites and/or locations (e.g., the location 108 and/or other locations, not shown).

According to some embodiments, the controller device 110 may store and/or execute specially programmed instructions (e.g., stored in the memory device 140, such as the AI module(s) 142) to operate in accordance with embodiments described herein. The controller device 110 may, for example, execute one or more programs, modules, and/or routines (e.g., the AI module(s) 142) that facilitate the autonomous and/or safe sterilization of the location 108 and/or the objects 120*a-n*, as described herein. According to some embodiments, the controller device 110 may comprise a computerized processing device, such as a centralized server utilized, for example, to (i) receive and/or identify data descriptive of the location 108 and/or of the objects 120*a-n*, e.g., from the sensor device 102, (ii) identify correlations between portions of received data and/or sensor readings and stored and/or learned object recognition and/or classification data, (iii) identify one or more of the objects 120*a-n*, (iv) classify the one or more of the objects 120*a-n*, (v) identify a sterilization trigger, (vi) identify a sterilization exception, (vii) identify a sterilization location(s), (viii) initiate sterilization processes (e.g., in a "safe" manner, as described herein), (ix) conclude or terminate a sterilization process, and/or (x) generate and/or transmit a report descriptive of sterilization activities, as described herein.

In some embodiments, the controller device 110, the sensor device 102, and/or the sterilization device 106 may be in communication with and/or comprise the memory device 140. The memory device 140 may comprise, for example, various databases and/or data storage mediums that may store, for example, image (and/or other sensor) data, object identification rules, object and/or material data, health data (e.g., safe UV and/or chemical exposure data), sterilization rule and/or scenario data, location data, cryptographic keys and/or data, login and/or identity credentials, and/or instructions (e.g., AI-based autonomous sterilization instructions and/or guidance, such as exemplified by the AI module(s) 142) that cause various devices (e.g., the sensor device 102 and/or the sterilization device 106) to operate in accordance with embodiments described herein.

The memory device 140 may store, for example, the AI module(s) 142, which may, when executed, facilitate and/or cause AI-based autonomous and/or "safe" sterilization, as described herein. In some embodiments, the memory devices 140 may comprise any type, configuration, and/or quantity of data storage devices that are or become known or practicable. The memory device 140 may, for example, comprise an array of optical and/or solid-state hard drives configured to store digital image and/or video data, image and/or object analysis data and/or location and/or object analysis data (e.g., analysis formulas and/or mathematical models), credentialing instructions and/or keys, and/or various operating instructions, drivers, etc. While the memory device 140 is depicted as a single stand-alone component of the controller device 110, the memory device 140 may comprise multiple components. In some embodiments, a multi-component memory device 140 may be distributed across various devices and/or may comprise remotely dispersed components. Any or all of the sensor device 102, the sterilization device 106, and/or the controller device 110 may comprise the memory device 140 or a portion thereof, for example.

Figure 2:
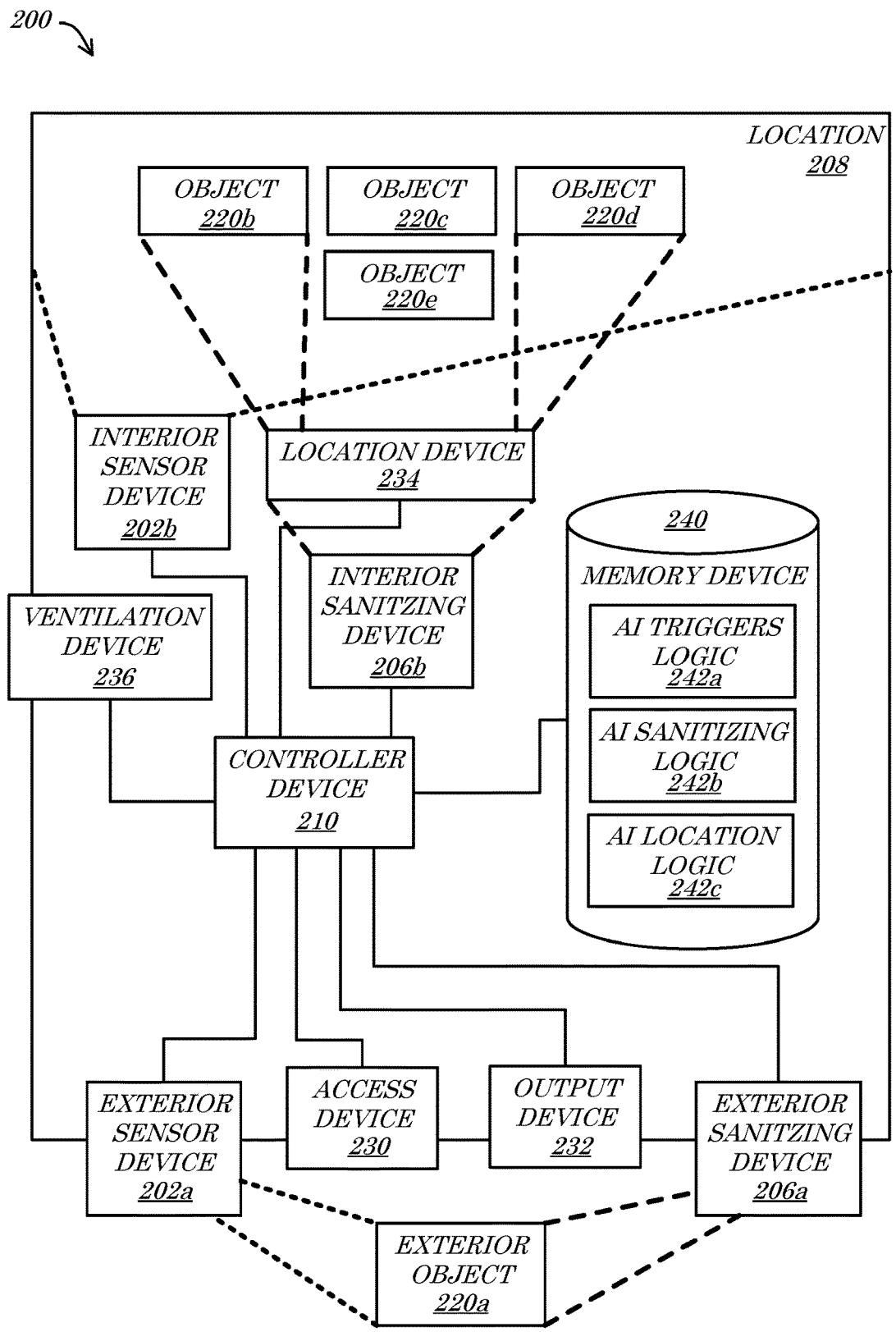
FIG. 2 is a block diagram of a safe sterilization system according to some embodiments.

Turning now to FIG. 2, a block diagram of a safe sterilization system 200 according to some embodiments is shown. In some embodiments, the safe sterilization system 200 may be similar in configuration and/or functionality to the system 100 of FIG. 1 herein. The safe sterilization system 200 may comprise, for example, a plurality of sensor devices 202a-b and/or a plurality of sanitizing devices 206a-b disposed at a location 208. In some embodiments, the location 208 may comprise an interior and an exterior and a first or exterior sensor device 202a may be coupled and/or oriented to acquire data descriptive of the exterior and/or a second or interior sensor device 202b may be coupled and/or oriented to acquire data descriptive of the interior. According to some embodiments, a first or exterior sanitizing device 206a may be coupled and/or oriented to emit sanitization substances to and/or effect sanitization of the exterior and/or a second or interior sanitizing device 206b may be coupled and/or oriented to emit sanitization substances to and/or effect sanitization of the interior.

In some embodiments, the safe sterilization system 200 may comprise a controller device 210 in communication with each of the sensor devices 202a-b and the sanitizing devices 206a-b. The controller device 210 may, for example, coordinate selective data acquisition and/or sterilization (or other sanitizing) of various objects 220a-e disposed in proximity to and/or in the location 208. According to some embodiments, one or more objects (e.g., a first or exterior object 220a) may be disposed in the exterior of the location 208 and/or one or more objects (e.g., the other or interior objects 220b-e) may be disposed in the interior of the location 208. The location 208 may comprise, for example, a building, vehicle, or other structure and/or enclosed (or enclosable) area. In some embodiments, the location 208 (and/or the safe sterilization system 200) may comprise an access device 230 such as a door that governs access and/or passage between the interior and the exterior of the location 208. According to some embodiments, the location 208 (and/or the safe sterilization system 200) may comprise an output device 232. The output device 232 may comprise, for example, a sign, speaker, screen, and/or other known or practicable output mechanism (or combinations thereof) coupled to provide output to either or both of the exterior and the interior of the location 208.

According to some embodiments, the safe sterilization system 200 may comprise a location device 234 coupled to provide and/or direct sterilization activities at the location 208. As depicted, for example, the location device 234 may be coupled to and/or be in communication with the interior sanitizing device 206b (and/or the controller device 210) to direct, steer, position, and/or otherwise cause application of sanitizing substances to certain and/or selective areas at the location 208. In some embodiments, such as in the case that a chemical sanitizing agent is utilized (e.g., emitted by the interior sanitizing device 206b), the controller device 210 may be in communication with and/or the location 208 (and/or the safe sterilization system 200) may comprise, a ventilation device 236. The ventilation device 236 may, for example, comprise a fan, duct work, drain, and/or other feature or object that is operable to be activated to circulate fluid (e.g., air and/or liquid) at the location 208. According to some embodiments, the ventilation device 236 may be configured to introduce fresh air (and/or liquid) into the interior of the location 208 and/or to expel air/gas (and/or liquid) from the interior of the location 208.

In some embodiments, the controller device 210 may be operable to execute stored instructions to selectively control, command, and/or interface with the various devices 202a-b, 206a-b, 230, 232, 234, 236. The controller device 210 may, for example, be in communication with (and/or comprise) a memory device 240 that stores one or more sets of coded instructions 242a-c. According to some embodiments, the coded instructions 242a-c may comprise AI triggers logic 242a, AI sanitizing logic 242b, and/or AI location logic 242c. The AI triggers logic 242a may, in some embodiments, cause and/or direct the controller device 210 to monitor one or more of the sensor devices 202a-b to identify a trigger condition. As described herein, other devices (such as a clock—not shown) may be communicated with and/or monitored to identify triggering conditions. In the case that a sanitizing process is scheduled to begin at certain times and/or upon expiration of certain time periods, for example, the controller device 210 may identify a triggering condition (in accordance with stored rules pursuant to the AI trigger logic 242a) based on time and/or based on sensor data received from one or more of the sensor devices 202a-b.

In the case that the exterior sensor device 202a detects the exterior object 220a in the exterior of the location 208 (and/or proximate to the location 208), for example, the exterior sensor device 202a may send one or more signals to the controller device 210 indicative and/or descriptive of the exterior object 220a. In accordance with the AI triggers logic 242a (and/or other instructions), the controller device 210 may analyze the data to identify the exterior object 210, classify the exterior object 210, and/or locate (or track) the exterior object 210. The controller device 210 may, by execution of the AI triggers logic 242a (and/or other instructions), for example, identify the exterior object 220a as a bench, chair, bus stop, trash/recycling can, water fountain, etc. In such a case, the AI triggers logic 242a may direct the controller device 210 to activate the exterior sanitizing device 206a to sanitize the exterior object 210. The exterior sanitizing device 206a, upon activation by the controller device 210 for example, may direct a sanitizing chemical agent and/or UV light toward the exterior object 210 to clean, sanitize, and/or sterilize the exterior object 210. According to some embodiments, the controller device 210 may, by execution of the AI triggers logic 242a (and/or other instructions), for example, identify the exterior object 220a as a human (e.g., a potential shopper, customer, student, passenger, etc., depending upon the context of the location 208). In some embodiments, the controller device 210 may execute the AI triggers logic 242a (and/or other instructions) to control the access device 230 and/or the output device 232, e.g., based on the identification and/or classification of the exterior object 220a.

The controller device 210 may, for example, cause a message, notice, and/or instructions to be output by the output device 232 and to the exterior object 220a (e.g., an identified human). According to some embodiments, the exterior object 220a may be informed that the location 208 is currently closed while an interior sterilization process is being executed. The access device 230 may be selectively and/or cooperatively controlled by the controller device 210 to remain closed, e.g., barring access of the interior of the location 208 to the exterior object 220a (e.g., until the interior sterilization process has been completed). In some embodiments, the output device 232 may be activated by the controller device 210 to output various messages and/or instructions to the exterior object 220a (and/or to the vicinity thereof) such as, but not limited to, a notification that the exterior object 220a and/or the area around the exterior object 220a is about to be sterilized (e.g., by the exterior sanitizing device 206a), a notification that the location 208 is closed for sanitizing, a notification of how much time remains until the sanitizing is complete, and/or a notification of instructions regarding entry conditions, rules, etc.

According to some embodiments, the controller device 210 may utilize the AI triggers logic 242a to initiate cleaning procedures in the interior of the location 208. The controller device 210 may execute the AI triggers logic 242a, for example, to determine that a scheduled time for an interior cleaning has arrived. In some embodiments, the controller device 210 may execute the AI sanitizing logic 242b to initiate the sanitizing procedure. According to some embodiments, the AI sanitizing logic 242b (and/or other rules) may cause the controller device 210 to identify an exception that pauses, suspends, ends, cancels, and/or delays the sanitizing procedure. In the example case depicted in FIG. 2, for example, before or at the time that the schedule-based trigger is identified, the controller device 210 may receive data from the interior sensor device 202b that indicates and/or describes second, third, and fourth objects 220b-d in the interior of the location 208. Trained AI object recognition logic and/or spatial recognition logic may be utilized, in some embodiments to classify and/or locate each of the second, third, and fourth objects 220b-d as objects that belong in the interior space and/or are fixed objects at the location 208 (e.g., chairs, tables, desks, counters, railings, etc.). According to some embodiments, in the case that the second, third, and fourth objects 220b-d are identified as background or static objects, there may be no exceptions and the controller device 210 may activate the interior sanitizing device 206b to sanitize the second, third, and fourth objects 220b-d (and/or the area(s) proximate thereto).

In some embodiments, such as in the case that a fifth object 220e is identified and/or detected, e.g., proximate to and/or in front of the third object 220c for example, the controller device 210 (e.g., executing the AI sanitizing logic 242b) may identify and/or compute an exception. The fifth object 220e may be identified and/or classified as a mobile and/or living object, for example, to which the sterilization process may be harmful. According to some embodiments, exceptions may be addressed in various manners. In the case that the interior sanitizing device 206b is capable of multiple types of sanitizing and/or cleaning, for example, the exception may trigger a switch from a first sanitizing method (e.g., UV light) to a second sanitizing method (e.g., dispersal of an airborne sanitizing mist that is not harmful to humans). In some embodiments, the exception may be addressed by adjusting the intensity (e.g., power), frequency (e.g., wavelength), type (e.g., UV-C, filter, chemical), duration (e.g., short bursts as opposed to longer emissions), and/or location of the sanitizing effort.

According to some embodiments, such as in the case that the location of the sanitizing effort is selected and/or adjusted due to an exception, the controller device 210 may command the location device 234 (e.g., in accordance with the AI location logic 242c (and/or other rules)) to direct, mask, steer, and/or otherwise limit the sanitizing emissions from the interior sanitizing device 206b to particular sub areas of the interior of the location 208. As depicted in FIG. 2, for example, and in the case where the fifth object 220e is identified and determined to not be a desirable candidate for sanitizing, the interior sanitizing device 206b may emit one or more sanitizing substances (e.g., liquids, gels, gases, solids, vapors, aerosols, UV light, heat, and/or other forms of radiation and/or energy) to and/or through the location device 234 which may direct and/or steer the emission(s) toward the second and fourth objects 220b, 220d (e.g., a subset of the interior objects 220b-e). In some embodiments, the third object 220c and/or the fifth object 220e may be specifically avoided to avoid or limit exposure, e.g., thereby increasing the "safeness" of the sanitizing procedure.

In some embodiments, such as in the case that one or more of the interior objects 220b-e are determined to be mobile and/or living objects, in the case that sanitizing is desired, the output device 232 may be activated to warn the interior objects 220b-e of an impending sanitizing procedure and/or may direct the interior objects 220b-e to exit the location 208. According to some embodiments, such as in the case that the location device 234 is utilized to selectively sanitize sub-areas and/or portions of the location 208, the message/ notice from the output device 232 may comprise instructions descriptive of those sub-areas and/or portions that should be avoided. In some embodiments, the access device 230 may comprise a plurality of gates, doors, windows, turnstiles, etc. that may be individually and/or collectively activated by the controlled device 210 to direct the interior objects 220b-e out of the location 208 and/or into sub-areas within the location 208 that are masked and/or protected, e.g., by steering, masking, filtering, and/or other location-based sanitizing emission manipulation provided by the location device 234.

In some embodiments, fewer or more components 202a-b, 206a-b, 208, 210, 220a-e, 230, 232, 234, 236, 240, 242a-c and/or various configurations of the depicted components 202a-b, 206a-b, 208, 210, 220a-e, 230, 232, 234, 236, 240, 242a-c may be included in the safe sterilization system 200 without deviating from the scope of embodiments described herein. In some embodiments, the components 202a-b, 206a-b, 208, 210, 220a-e, 230, 232, 234, 236, 240, 242a-c may be similar in configuration and/or functionality to similarly named and/or numbered components as described herein. In some embodiments, the safe sterilization system 200 (and/or portion and/or component 202a-b, 206a-b, 208, 210, 220a-e, 230, 232, 234, 236, 240, 242a-c thereof) may be utilized in accordance with the methods 500, 600 of FIG. 5 and/or FIG. 6 herein, and/or portions or combinations thereof.

Figure 3:
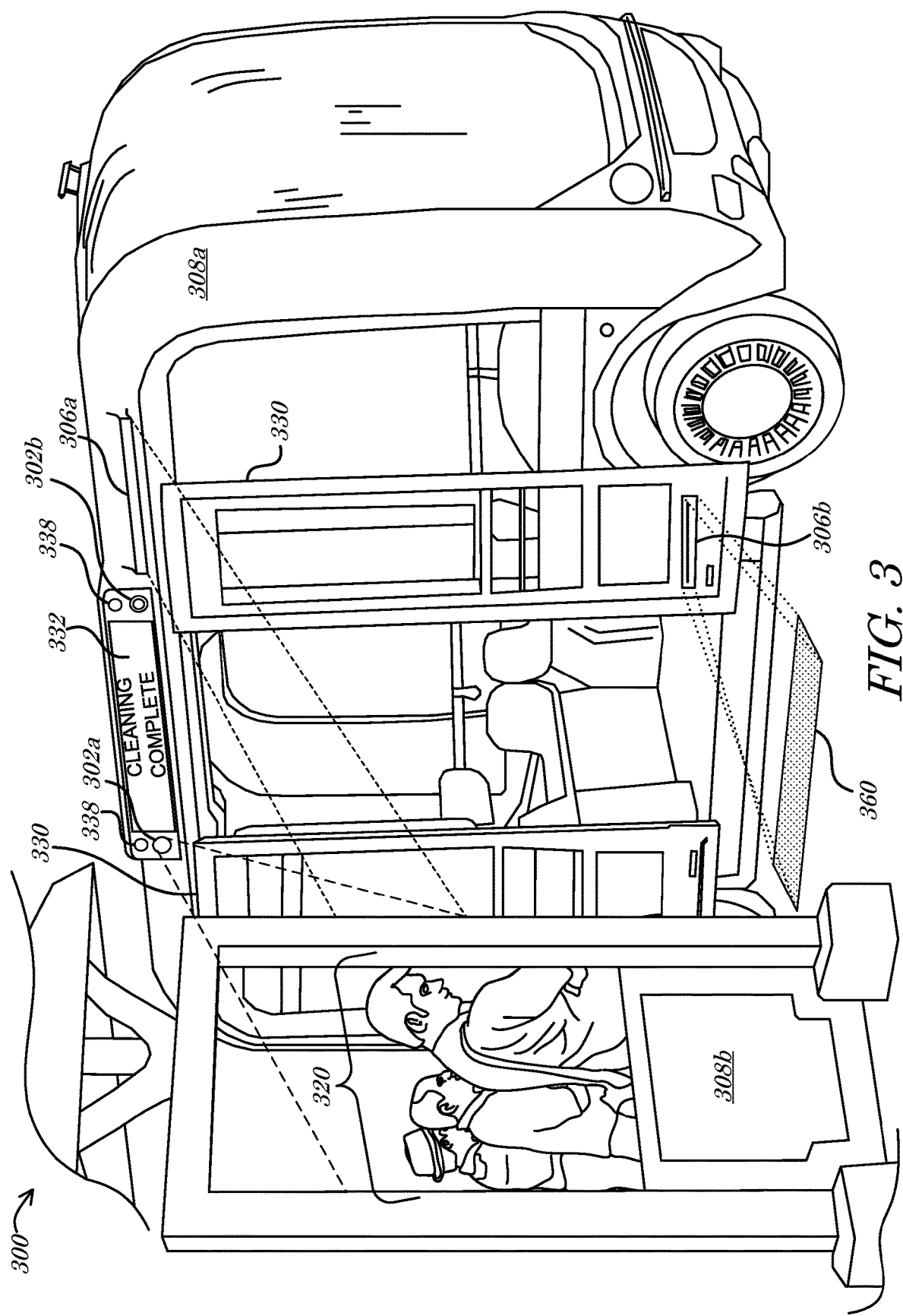
FIG. 3 is a perspective diagram of a safe sterilization system according to some embodiments.

Referring now to FIG. 3, a perspective diagram of a safe sterilization system 300 according to some embodiments s shown. In some embodiments, the safe sterilization system 300 may be similar in configuration and/or functionality to the systems 100, 200 of FIG. 1 and/or FIG. 2 herein. The safe sterilization system 300 may comprise, for example, a plurality of sensor devices 302a-b and/or a plurality of sanitizing devices 306a-b disposed proximate to and/or at one or more locations 308a-b. In some embodiments, the a first location 308a may comprise an autonomous vehicle (e.g., comprising and/or defining an interior and an exterior) and/or a second location 308b may comprise a bus stop at which the autonomous vehicle 308a has stopped. According to some embodiments, the plurality of sensor devices 302a-b and/or the plurality of sanitizing devices 306a-b may be mounted on and/or coupled to the autonomous vehicle 308a. The sensor devices 302a-b may be coupled and/or oriented to acquire data descriptive of the exterior area adjacent to the autonomous vehicle 308a, for example, and/or the plurality of sanitizing devices 306a-b may be coupled and/or oriented to emit sanitization substances to and/or effect sanitization of the exterior area adjacent to the autonomous vehicle 308a. In the case that the autonomous vehicle 308a is located at the bus stop 308*b*, the exterior area adjacent to the autonomous vehicle 308*a* may comprise the bus stop 308*b*.

According to some embodiments, the sensor devices 302*a-b* may comprise different types of sensors. A first sensor device 302*a* may comprise a camera and/or imaging device, for example, and/or a second sensor device 302*b* may comprise a temperature sensor, thermal imaging device, etc. In some embodiments, the sensor devices 302*a-b* may be utilized to provide data to a processing device (not shown) such that data descriptive of the autonomous vehicle 308*a*, the bus stop 308*b*, and/or the areas adjacent thereto may be utilized for various purposes. The first sensor 302*a* may, for example, capture images of the bus stop 308*b* that are utilized to identify, detect, locate, and/or track one or more people 320 (e.g., at the bus stop 308*b*, as shown). According to some embodiments, the safe sterilization system 300 may learn which objects visible in images of the bus stop 308*b* are fixed (e.g., due to repetitively being in the same position at various sample/image times; e.g., background or baseline objects) and may accordingly be capable or readily identifying and/or classifying objects that differ from the typical set of objects (e.g., the people 320). In some embodiments, the identification of the people 320 may cause the safe sterilization system 300 to forgo cleaning operations at the bus stop 308*b*. Such operations may be delayed, for example, until all people 320 have left the bus stop 308*b* (and/or a different bus stop—not separately depicted—is arrived at and is determined to have no people 320). According to some embodiments, such as in the case that an inside area of the autonomous vehicle 308*a* is being sanitized (e.g., as described herein), the safe sterilization system 300 may close (or maintain in a closed position) one or more doors 330 of the autonomous vehicle 308*a* to prevent the people 320 from entering the autonomous vehicle 308*a* (e.g., which may be unsafe due to use of harmful chemicals, heat, and/or radiation). According to some embodiments, once such cleaning is complete, the doors 330 may be opened and/or an output device 332 may be utilized to notify the people 320 that they may now enter the autonomous vehicle 308*a* (e.g., "cleaning complete").

In some embodiments, the second sensor device 302*b* may be utilized to screen the people 320 and/or to monitor the bus stop 308*b*. In the case that the second sensor device 302*b* comprises a temperature sensing device, for example, the second sensor device 302*b* may capture temperature data descriptive of one or more of the people 320. According to some embodiments, the temperature data may be utilized to determine whether to open the doors 330. In the case that an elevated (e.g., above a stored threshold) temperature is detected, for example, the doors 330 may be closed (or kept closed) such that a potentially infected/sick person 320 does not enter the autonomous vehicle 308*a*. In some embodiments, the output device 332 may be utilized to notify the people 320 (and/or a particular person 320) of the temperature reading and/or may provide instructions, such as "please see your doctor", "please distance from others", etc. According to some embodiments, the doors 330 may only be opened after a person 320 performs a certain task such as confirming their identify, confirming or verifying a vaccination status (e.g., presenting, scanning, a vaccination record card), confirming and/or verifying a travel status (e.g., verified by accessing a centralized travel database; not shown), putting on a mask, and/or sanitizing their hands (e.g., via a sanitizing dispenser of the autonomous vehicle 308*a*; not shown).

In some embodiments, the safe sterilization system 300 may comprise one or more illumination devices 338 coupled and/or oriented to illuminate the bus stop 308*b* and/or the people 320. Illumination may facilitate, for example, the capturing of data by one or more of the sensor devices 302*a-b*. According to some embodiments, the illumination may comprise simple visible light, IR or near-IR light, and/or other types and/or combinations of illumination that are or become known or practicable. According to some embodiments, the illumination devices 338 may comprise and/or be combined with one or more of the sanitizing devices 306*a-b*. In the case that a sanitizing device 306*a-b* comprises a UV illumination device, for example, it may comprise one or more of the illumination devices 338 and/or a single combined device may be capable of emitting various frequencies, wavelengths, and/or magnitudes (e.g., amplitudes) of radiation (e.g., visible and/or not visible).

According to some embodiments, the sanitizing devices 306*a-b* may be selectively activated based on data received from one or more of the sensor devices 302*a-b*. In the case that the people 320 have left the bus stop 308*b* and/or have boarded the autonomous vehicle 308*a* (such situation not depicted), for example, the safe sterilization system 300 may determine that it has become safe to sanitize the bus stop 308*b* and may accordingly activate a first sanitizing device 306*a* directed toward the bus stop 308*b*. In some embodiments, the first sanitizing device 306*a* may dispense a sanitizing substance toward the bus stop 308*b*. Various chemical sprays, heat, and/or UV light may be utilized, for example, to sanitize the bus stop 308*b* and/or surfaces and/or objects thereof. In some embodiments, the sensor devices 302*a-b* may monitor the bus stop 308*b* to ensure that no people 320 enter the area being cleaned. In the case that movement of a person 320 and/or other animal into the bus stop 308*b* is detected or is detected to be imminent (e.g., by tracking movement of objects near the bus stop 308*b*), the sanitizing operation may be stopped and/or paused (e.g., to maintain the safety of the living object).

In some embodiments, the sanitizing devices 306*a-b* may be oriented and/or coupled to sanitize particular regions, areas, and/or objects. The first sanitizing device 306*a* may comprise a chemical mister and/or chemical foam spray dispenser, for example, that is oriented to mist/spray the bus stop 308*b* with a cleaning chemical. In such a case, it may be desirable to ensure that the people 320 are not situated at the bus stop 308*b* prior to commencing such a cleaning operation. According to some embodiments, a second sanitizing device 306*b* may comprise a UV (and/or other sterilizing) light emitter that is oriented to direct UV radiation to specific sub-areas of the bus stop 308*b* and/or other areas adjacent to the autonomous vehicle 308*a*. As depicted in FIG. 3, for example, the second sanitizing device 306*b* may be directed to sanitizing a ground surface in front of (e.g., adjacent to) the doors 330. The second sanitizing device 306*b* may, in some embodiments, emit light (and/or another substance and/or sanitizing element) that covers a treatment area 360 that is likely to be stepped on or in by the people 320 as they enter the autonomous vehicle 308*a* (e.g., via the doors 330). According to some embodiments, even in the case that the people 320 are detected at the bus stop 308*b* and/or entering the autonomous vehicle 308*a*, the second sanitizing device 306*b* may be activated, e.g., to sterilize the shoes of the people 320. Because UV light is generally not a health risk for areas of the body covered by clothing (e.g., shoes and/or socks), for example, the second sanitizing device 306*b* may be activated without causing harm to the people 320. Because UV light may be harmful to uncovered feet (e.g., in the case one or more of the people 320 are barefoot or are wearing sandals, for example) and/or to other parts of the body, however, the safe sterilization system 300 may analyze the people 320 (e.g., via the sensor devices 302a-b) to verify that proper footwear is being worn and/or to ensure that the second sanitizing device 306b is promptly disengaged in the case that one of the people 320 falls, bends down, and/or otherwise advances a susceptible body part toward the treatment area 360 (and/or toward an irradiated area between the treatment area 360 and the emitter of the second sanitizing device 306b).

In some embodiments, fewer or more components 302a-b, 306a-b, 308a-b, 320, 330, 332, 338, 360 and/or various configurations of the depicted components 302a-b, 306a-b, 308a-b, 320, 330, 332, 338, 360 may be included in the safe sterilization system 300 without deviating from the scope of embodiments described herein. In some embodiments, the components 302a-b, 306a-b, 308a-b, 320, 330, 332, 338, 360 may be similar in configuration and/or functionality to similarly named and/or numbered components as described herein. In some embodiments, the safe sterilization system 300 (and/or portion and/or component 302a-b, 306a-b, 308a-b, 320, 330, 332, 338, 360 thereof) may be utilized in accordance with the methods 500, 600 of FIG. 5 and/or FIG. 6 herein, and/or portions or combinations thereof.

Figure 4:
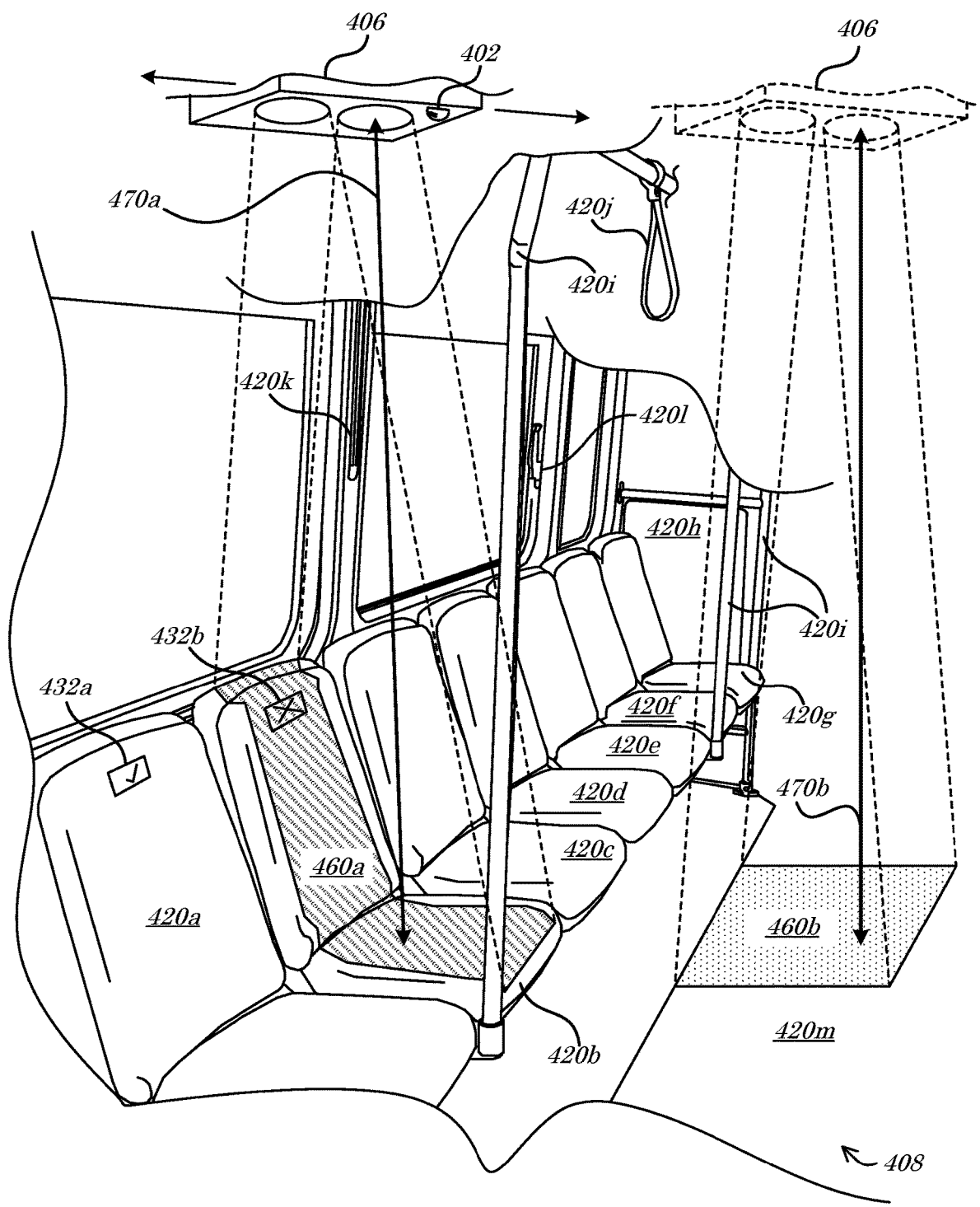
FIG. 4 is a perspective diagram of a safe sterilization system according to some embodiments.

Turning now to FIG. 4, a perspective diagram of a safe sterilization system 400 according to some embodiments s shown. In some embodiments, the safe sterilization system 400 may be similar in configuration and/or functionality to the systems 100, 200, 300 of FIG. 1, FIG. 2, and/or FIG. 3 herein. The safe sterilization system 400 may comprise, for example, a sensor 402 and/or a sterilizing device 406 disposed at or in a location 408—e.g., an inside of a transit vehicle, such as a passenger compartment, as depicted for non-limiting purposes of example. In some embodiments, the sensor 402 may be utilized to ensure that the passenger compartment 408 is empty and/or that certain portions of the passenger compartment 408 are not occupied, e.g., prior to commencing sterilization operations. According to some embodiments, the sterilizing device 406 may comprise a plurality of sterilization emitters disposed throughout the passenger compartment 408 and/or may comprise a moveable device. The sterilizing device 406 may be mounted on a track, wires, and/or rail (not shown), for example, and/or may otherwise be capable of translational and/or rotational movement such that it may be selectively positioned to sterilize particular areas, sub-areas, and/or sub-portions of the passenger compartment 408. As depicted in FIG. 4, the sensor 402 may be mounted and/or coupled to the sterilizing device 406 such that it too is moveable, e.g., with the sterilizing device 406. In some embodiments, the sensor 402 may be statically mounted and/or may be separately moveable and/or capable or re-orientation (e.g., pan and/or tilt capabilities). The senor 402 may also or alternatively comprise a plurality of different sensors disposed throughout the passenger compartment 408 such as various cameras, temperature sensors, pressure sensors (e.g., seat and/or floor sensors), ranging sensors (e.g., LiDAR, acoustic, etc.), movement sensors, etc.

According to some embodiments, the passenger compartment 408 may comprise various objects 420a-m that may be sterilized by the sterilizing device 406 (e.g., in a safe manner, such as in the case that no passengers are detected by the sensor 402). In some embodiments, different objects 420a-m may be sterilized in different manners, e.g., in accordance with stored sterilization rules and/or AI logic. The locations of the various objects 420a-m in the passenger compartment 408 may be pre-programmed, in some embodiments (such as based on blueprints and/or designs for the vehicle), and/or may be derived and/or learned utilizing AI-based object recognition, classification, and/or location sensing (e.g., ranging). According to some embodiments, the various objects 420a-m may be identified and/or classified such that different characteristics of the various objects 420a-m may be taken into account by the safe sterilization system 400 to vary the sterilization process for the passenger compartment 408. Characteristics of various types of objects such as which material(s) they are made from, colors, light absorbance characteristics, liquid absorbance characteristics, smoothness (or roughness), hardness, and/or durability (general and/or with respect to certain stresses such as chemical or UV light exposure) may, for example, be stored in a database (not shown) and cross-referenced with the identified types and/or classifications of the objects 420a-m to identify and/or determine characteristics of the various objects 420a-m in the passenger compartment 408.

In some embodiments, the sterilizing device 406 may sterilize, sanitize, and/or clean any or all of the various objects 420a-m in the passenger compartment 408 in a variety of manners, e.g., based on characteristics of the various objects 420a-m. In the case of passenger seats 420a-g, for example, the sterilizing device 406 may emit UV light to sterilize seat surfaces thereof. According to some embodiments, a first seat 420a may comprise a first output device 432a that indicates that the first seat 420a is safe to sit in, available, and/or has already been sanitized. In some embodiments, a second seat 420b may comprise a second output device 432b that indicates that the second seat 420b is not safe to sit in, not available, and/or is currently being sanitized (e.g., as depicted). According to some embodiments, the sterilizing device 406 may emit a sanitizing substance across the surface of the second seat 420b, as shown, thereby defining a first treatment area 460a. In some embodiments, the substance applied to the first treatment area 460a (e.g., UV light) may comprise a first substance and/or sterilization method that may be selected from a plurality of available substances/methods based on characteristics of the second seat 420b. It may be determined (e.g., based on the stored rules), for example, that the second seat 420b is covered in a fabric that is UV resistant but that is susceptible to staining from chemical treatment options. In accordance with some embodiments, UV light may be selected as the sterilizing substance to be applied to the first treatment area 460a. In some embodiments, parameters of the applied method may be set and/or selected based on characteristics of the second seat 420b. It may be known, for example, that the UV resistance of the fabric covering is rated for a maximum strength and/or exposure duration, and the strength and/or duration of the applied sanitizing light may accordingly be set to values beneath the maximum thresholds (e.g., to minimize potential damage to the second seat 420b).

According to some embodiments, different seats 420a, 420c-g may be treated by different means and/or utilizing different parameter value settings such as high emitting power, different frequencies, wavelengths, and/or different exposure durations and/or intensities. The first seat 420a may comprise a fold-up handicapped area seat that comprises a plastic surface, for example, and may accordingly accept higher levels and/or durations of UV sterilization than the fabric-covered second seat 420b. In some embodiments, other objects 420h-m may be selectively treated utilizing different methods, substances, and/or settings. The passenger compartment 408 may comprise, in some embodiments, a hard-plastic divider 420h, handrails 420i, hand straps 420j, a stop indicator device 420k, an emergency exit handle 420*l* (and/or other handle), and/or a floor surface 420*m*. According to some embodiments, due to the high frequency of expected use and exposure to contaminants, the handrails 420*i* and hand straps 420*j* may be sprayed, by the sterilizing device 406, with a sterilizing agent (e.g., liquid or foam). In some embodiments, a low likelihood of direct contact and a durable hard surface may qualify the hard-plastic divider 420*h* for a misting of sterilizing agent of a higher strength and/or lower level of dilution and/or may warrant a shorter duration of exposure. In some embodiments, the floor surface 420*m* may be sterilized utilizing a different wavelength or frequency of light emission and/or may be more intensely saturated (e.g., higher intensity and/or longer duration) than the seats 420*a-g*, e.g., defining a second treatment area 460*b*.

In some embodiments, other factors may be considered by the safe sterilization system 400 in determining sterilization process parameter values. As depicted in FIG. 4, for example, the second seat 420*b* may be disposed and/or situated at a first distance 470*a* from the sterilizing device 406 (e.g., at a first position of the sterilizing device 406 and/or at a first time) and/or the floor surface 420*m* may be disposed and/or situated at a second distance 470*b* from the sterilizing device 406 (e.g., at a second position of the sterilizing device 406 and/or at a second time). According to some embodiments, the distances 470*a-b* may be utilized to calculate the parameter values required to achieve a desired sterilization level of the respective second seat 420*b* and floor surface 420*m*. In some embodiments, a desired level of sanitizing may be computed based on characteristics of the objects 420*a-m*, the distances 470*a-b* to the objects 420*a-m* may be identified (e.g., utilizing data from the sensor 402), and given the measured distances 470*a-b* and/or other parameters (e.g., time since last cleaning, number of passengers since last cleaning, pandemic threat level, measured levels of contamination, humidity, temperature, etc.) a target type, strength, duration, and/or frequency (e.g., time-based frequency) may be computed for the sterilization process.

According to some embodiments, the sterilizing device 406 may move about the passenger compartment 408 and/or direct the sanitizing substances toward the various objects 420*a-m* and switching sterilization methods, types, substances, and/or settings for any particular object 420*a-m* currently being sanitized. The sterilizing device 406 may sterilize the first treatment area 460*a* at a first time, from a first position, utilizing a first sterilization type/method/substance, and/or utilizing first settings, for example, and/or may sterilize the second treatment area 460*b* at a second time, from a second position, utilizing a second sterilization type/method/substance, and/or utilizing second settings. In some embodiments, such as in the case that the sterilizing device 406 comprises a plurality of emitters disposed throughout the passenger compartment 408, such plurality of emitters may be selectively and coordinatingly activated to achieve the computed sterilization results. According to some embodiments, one or more location devices (not shown) such as beam steering devices, masking devices, and/or other direction and/or area-limiting devices may be employed to cause the emitted substances to be applied to the desired treatment areas 460*a-b*.

In some embodiments, fewer or more components 402, 406, 408, 420*a-m*, 432*a-b*, 460*a-b*, 470*a-b* and/or various configurations of the depicted components 402, 406, 408, 420*a-m*, 432*a-b*, 460*a-b*, 470*a-b* may be included in the safe sterilization system 400 without deviating from the scope of embodiments described herein. In some embodiments, the components 402, 406, 408, 420*a-m*, 432*a-b*, 460*a-b*, 470*a-b* may be similar in configuration and/or functionality to similarly named and/or numbered components as described herein. In some embodiments, the safe sterilization system 400 (and/or portion and/or component 402, 406, 408, 420*a-m*, 432*a-b*, 460*a-b*, 470*a-b* thereof) may be utilized in accordance with the methods 500, 600 of FIG. 5 and/or FIG. 6 herein, and/or portions or combinations thereof.

III. Autonomous Sterilization Methods

Figure 5:
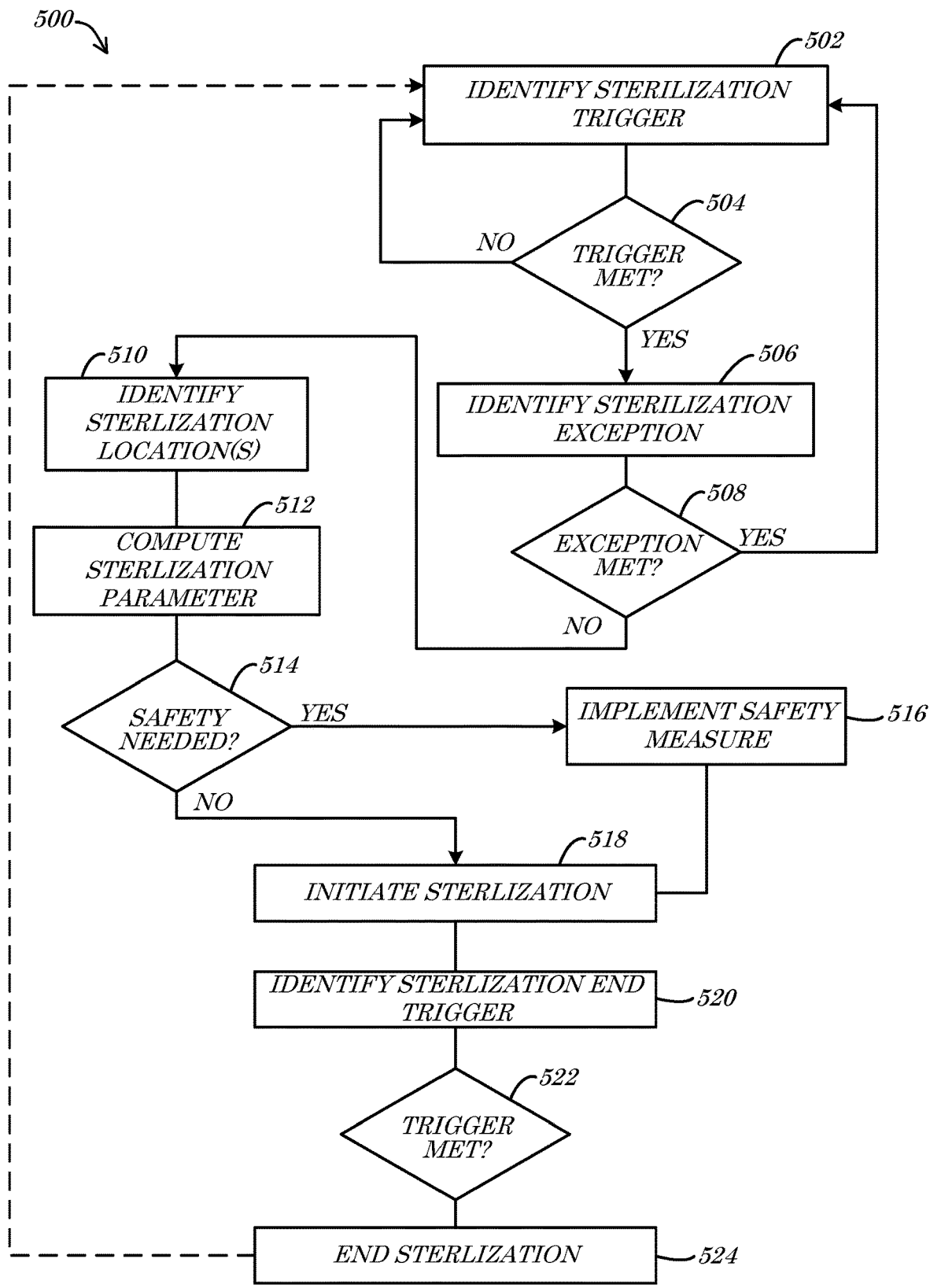
FIG. 5 is a flow diagram of a method according to some embodiments.

Turning to FIG. 5, a flow diagram of a method 500 according to some embodiments is shown. In some embodiments, the method 500 may be performed and/or implemented by and/or otherwise associated with one or more specialized and/or specially-programmed computers (e.g., the controller devices 110, 210, 610, the sensor devices 102, 202*a-b*, 302*a-b*, 402, 602, and/or the sanitizing/sterilizing/emitting devices 106, 206*a-b*, 306*a-6*, 406, 606*a-c* of FIG. 1, FIG. 2, FIG. 3, FIG. 4, and/or FIG. 6 herein), computer terminals, computer servers, computer systems and/or networks, and/or any combinations thereof. In some embodiments, the method 500 may be embodied in, facilitated by, and/or otherwise associated with various input mechanisms and/or interfaces and/or may be effectuate by the execution of one or more stored programs, modules, routines, rule sets, and/or logical steps, e.g., as defined by one or more AI programs and/or modules (e.g., the AI module(s) 142, AI logic 242*a-c*, and/or the instructions 742-1, 742-2 of FIG. 1, FIG. 2, and/or FIG. 7 herein).

The process diagrams and flow diagrams described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure. Any of the processes and methods described herein may be performed and/or facilitated by hardware, software (including microcode), firmware, or any combination thereof. For example, a storage medium (e.g., a hard disk, Random Access Memory (RAM) device, cache memory device, Universal Serial Bus (USB) mass storage device, and/or Digital Video Disk (DVD); e.g., the memory devices 140, 240, 740, 840*a-e* of FIG. 1, FIG. 2, FIG. 7, FIG. 8A, FIG. 8B, FIG. 8C, FIG. 8D, and/or FIG. 8E herein) may store thereon instructions that when executed by a machine (such as a computerized processor) result in performance according to any one or more of the embodiments described herein.

In some embodiments, the method 500 may comprise identifying (e.g., by an electronic processing device and/or by executing an AI logic routine) a sterilization trigger, at 502. One or more trigger conditions, thresholds, rules, and/or logic may be stored in a memory device, for example, and may be accessed in accordance with executed instructions. According to some embodiments, a sanitizing trigger may comprise, but may not be limited to, a time trigger, an occupancy trigger, a location trigger, a third-party data trigger, and/or a sensor reading trigger. Sterilization may be triggered, for example, upon expiration of a particular time period (e.g., an amount of time elapsed since a previous sterilization), in accordance with a predetermined schedule (e.g., at a particular time, day, day of the week, time of day (e.g., night, day), time of year, season), upon detection of an object (e.g., a human, pet/service animal), upon a negative determination of living object presence (e.g., no pets/animals and/or humans), upon passage/usage of/by a predetermined number of people/passengers, upon detection of a certain temperature, humidity level, other weather event, threat level, travel restrictions, bacteria and/or virus detection, and/or upon a mobile location/object moving to, from, and/or through a particular geographic area and/or location. A vehicle capable of autonomous sterilization may, in some embodiments, achieve a trigger condition be performing a predetermined number of stops, traveling a predefined number of miles, being in operation for a predetermined amount of time, transporting a predetermined number of passengers (and/or cargo items), and/or arriving at a particular destination. In some embodiments, location information may be determined from GPS data, signal triangulation data, and/or inertial data.

According to some embodiments, the method 500 may comprise determining (e.g., by the electronic processing device and/or by executing the AI logic routine) whether the sterilization trigger is met (or satisfied), at 504. One or more parameter values may be compared to stored values in accordance with the trigger to determine whether a match and/or threshold exceed condition exists, for example. In the case that one hundred (100) passengers have been counted (e.g., by a sensor device) as having been transported since a previous sterilization process, for example, a passenger volume trigger may be met/satisfied. According to some embodiments, in the case that a time-based window and/or elapsed time exceeds a threshold value (e.g., with respect to a reference time such as the current time), the trigger may be met. In accordance with some embodiments, in the case that a sensor fails to detect a human and/or provides data suggesting that any or all humans (or other living objects) have left an area, the trigger may be met. According to some embodiments, multi-tier trigger conditions may be implemented. An autonomous vehicle may trigger sterilization upon completion of a minimum number of stops but only when it is next determined to be empty, for example. Other combinations of two or more trigger conditions may be implemented in some embodiments.

In some embodiments, the method 500 may comprise identifying (e.g., by the electronic processing device and/or by executing the AI logic routine) a sterilization exception, at 506. One or more exception conditions, thresholds, rules, and/or logic may be stored in a memory device, for example, and may be accessed in accordance with executed instructions. According to some embodiments, an exception condition may comprise, but may not be limited to, detection of living object presence at the location, a current location, a current time, occupancy and/or use metrics, sterilizing substance availability, and/or available power/fuel levels. While sterilization may be triggered to automatically occur every hour (i.e., a time-based sterilization trigger), for example, an exception may be programmed to occur in the case that humans/passengers are present at the location (e.g., inside of a vehicle, building, and/or at a bus stop and/or other outside location). Triggers and exceptions may be hard-coded to create a complex logic web of conditional rules for conducting autonomous sterilization processes and/or may be defined dynamically by an autonomous system utilizing AI training and logic.

According to some embodiments, the method 500 may comprise determining (e.g., by the electronic processing device and/or by executing the AI logic routine) whether the sterilization exception is met (or satisfied), at 508. One or more parameter values may be compared to stored values in accordance with the exception condition to determine whether a match and/or threshold exceed condition exists, for example. In the case that sensor image data is analyzed to identify a seventy-percent (70%) confidence level for the presence of a human at the location, for example, human presence exception condition may be met/satisfied. According to some embodiments, in the case that a power (e.g., battery power) level falls below a predefined threshold (e.g., twenty percent (20%)), a low power exception may exist. According to some embodiments, a measured and/or estimated amount of sanitizing substance remaining, e.g., a remaining quantity of sanitizing chemical liquid and/or foam may be compared to a minimum threshold to determine, allocate, ration, and/or otherwise manage the interaction of triggers and exceptions to conserve the remaining stores.

In some embodiments, the method 500 may comprise identifying (e.g., by the electronic processing device and/or by executing the AI logic routine) a sterilization location, at 510. According to some embodiments, an entire location such as an entire area that is within an operational range of a sterilization emitter may be automatically selected and/or defined. In some embodiments, such as in the case that an emitter is moveable and/or multiple emitters are available for selection, one or more areas and/or sub-areas of the location may be identified. Each emitter of a plurality of emitters at a location may be oriented and/or coupled to sanitize a particular sub-area at the location, for example, and/or a moveable emitter may be capable of sanitizing multiple sub-areas (e.g., at different times and positions). According to some embodiments, one or more sub-areas may be identified based on sensor readings and/or data. In the case that a human (and/or other living object) is identified (e.g., as an exception), for example, the location of the human may be selected as a sub-area or may be specifically excluded or subtracted from the total area to determine a masking area (e.g., an area to be masked or otherwise avoided). In some embodiments, sub-areas and/or locations for sterilization may be identified and/or selected based on measured usage (e.g., number of passengers having used a particular seat) and/or based on sensor readings. A temperature sensor may be utilized in some embodiments, for example, to identify one or more sub-areas that have temperatures below or above one or more thresholds. Low temperatures may indicate lower usage, no recent usage (e.g., a cold seat may not have been recently used), or may indicate that a current sterilization process has not yet achieved a desired exposure level for a particular surface, object, and/or sub-area. High temperatures may indicate recent usage, bacterial and/or viral activity, or may indicate that a current sterilization process has achieved a desired level of exposure. According to some embodiments, such temperature readings may be utilized to generate and/or define a map of the location (e.g., a heat map) that may be utilized to identify certain portions of the location that require sterilization.

According to some embodiments, the method 500 may comprise computing (e.g., by the electronic processing device and/or by executing the AI logic routine) a sterilization parameter, at 512. One or more sterilization devices may, for example, be capable of adjustable parameter settings and/or values and may be dynamically and/or autonomously set based on various variables, rules, and/or logic. In the case that a human (or other living object) is detected in an area, for example, a safer sterilizing method may be selected (e.g., from a plurality of available methods), a lower power setting may be utilized, and/or a shorter duration of sterilization may be effectuated. An autonomous sterilization system may, in some embodiments, dynamically select and/or calculate one or more parameter values to customize the sterilization of any particular location, sub-area, and/or object (or even a particular portion of an object—such as a person's feet or shoes). According to some embodiments, a database and/or other stored repository of object characteristics may be consulted (e.g., accessed and/or queried) to determine how various sterilization parameter values should be set. UV radiation wavelength, frequency, intensity, and/or duration may be adjusted, for example, based on the known (and/or estimated—e.g., based on AI object recognition) material, distance, temperature, hardness, and/or other characteristic of a target location, sub-area, object, etc. A more diluted or less concentrated chemical cleaning agent may be utilized (and/or prepared or mixed), in some embodiments, for sterilization in the presence of living objects and/or for objects that otherwise may be adversely affected by stronger chemical compositions.

In some embodiments, the method 500 may comprise determining (e.g., by the electronic processing device and/or by executing the AI logic routine) whether safety measures are needed, at 514. Detection of an exception may, in some embodiments, require various levels of safety in accordance with a desired safety protocol for a particular location. In the case of a smaller enclosed space such as an interior of an autonomous shuttle bus, for example, sterilization may be delayed, paused, and/or stopped unless and/or until no humans are detected. In such embodiments, a safety measure may comprise the delaying, pausing, and/or stopping and/or may comprise a closing and/or locking of an access device, e.g., to prevent passengers from entering during the sterilization process. According to some embodiments, a safety measure may comprise selective sterilization of the identified sub-areas. It may be determined, for example, that a single passenger is sitting in a particular seat and the safety measure may comprise directing sterilization to other areas of the location that do not include the seat and/or that are distant from the seat by a factor of safety (e.g., sterilization may not occur within two feet (2-ft) of the seat and/or the passenger. In some embodiments, safety measures may include, but are not limited to, outputting notifications and/or warnings (e.g., displaying messages, flashing lights, sounding a warning alarm), controlling access devices, controlling ventilation devices, activating a location masking/limiting device, According to some embodiments, the method 500 may comprise implementing (e.g., by the electronic processing device and/or by executing the AI logic routine) a safety measure, at 516. In the case that the safety measure comprises delaying, pausing, and/or stopping sterilization, one or more emitters may be turned off and/or redirected. In the case that sterilization processes may still occur, but in a limited fashion, one or more identified safety measures such as shielding, substance steering, and/or warnings may be implemented. According to some embodiments, a plurality of safety measures may be combined to define a particular safety measure. In the case that a human is detected at a particular sub-area of a location, for example, the implementation of the safety measure may comprise warning the human to remain in the current sub-area, activating sterilization devices in other sub-areas, activating a ventilation system (e.g., to reduce the potential for migration of liquid and/or aerosol chemical agents from entering the current sub-area of the human), and/or restricting access to other areas (e.g., by controlling one or more access devices).

In some embodiments, the method 500 may comprise initiating (e.g., by the electronic processing device and/or by executing the AI logic routine) sterilization (and/or sanitizing or otherwise cleaning), at 518. In the case that the safety measure comprise delaying, pausing, and/or stopping sterilization, once the delay, pause, and/or stop-order has expired, elapsed, and/or ended, sterilization may begin (e.g., presuming there are no additional exceptions requiring no-sanitize safety measures). In any case, once sterilization has been triggered and is permitted to occur, one or more sterilization emitters (e.g., chemical emitters, UV light emitters), filters, and/or other devices may be actuated to begin sterilization. In some embodiments, sterilization may occur in accordance with any parameter value settings computed and/or selected, e.g., for the particular location, sub-area, and/or object being sterilized. In some embodiments, sterilization may occur in different phases or stages. In the case that different types of sterilization, different settings, and/or different sub-areas are to be sterilized, for example, different sterilization sub-processes may be executed and/or initiated for each such sterilization type, setting, sub-area, and/or object. In the case of a single moveable (e.g., steerable and/or translationally and/or rotationally moveable) sterilization device, the different stages may coincide with and/or define different positions and/or different times. The device may utilize a first setting at a first position and a first time, for example, and may be switched to use a different or second setting at a second position and a second time.

According to some embodiments, the method 500 may comprise identifying (e.g., by an electronic processing device and/or by executing an AI logic routine) a sterilization end trigger, at 520. In some embodiments, a sterilization end trigger may comprise an identification of an exception trigger being met. In the case that a human enters an area being sterilized (and/or an area within a defined safety range thereof), for example, it may be desirable to end the sterilization (or to modify settings thereof). According to some embodiments, an end trigger may be based upon sensor readings and/or data. Sterilization utilizing UV light may be known to increase the temperature of a surface to a certain level once a desired exposure/treatment level has been reached, for example, and a temperature threshold may accordingly be set to determine when the desired exposure level has been met. According to some embodiments, a desired sanitizing exposure for a given sterilization type and setting may be known to be reached after a duration of application and an expiration of a predefined time period may accordingly comprise an end trigger.

In some embodiments, the method 500 may comprise determining (e.g., by the electronic processing device and/or by executing the AI logic routine) whether the sterilization end trigger is met (or satisfied), at 522. One or more parameter values may be compared to stored values in accordance with the end trigger condition to determine whether a match and/or threshold exceed condition exists, for example. In the case that a difference between a current time and the time that sterilization was initiated is greater than or equal to a predetermined sterilization duration, for example, the end trigger may be met. In some embodiments, various end triggers may need to be satisfied to meet the end trigger condition. According to some embodiments, multiple possible end triggers may exist and the triggering of any one of the end triggers may cause the end trigger condition to be met.

According to some embodiments, the method 500 may comprise ending (e.g., by an electronic processing device and/or by executing an AI logic routine) the sterilization, at 524. Any sterilization emitters and/or devices (e.g., filters) may, for example, be deactivated, e.g., upon satisfaction of one or more end trigger conditions. In such a manner, for example, a system may autonomously sterilize one or more locations, sub-areas, and/or objects in a safe manner.

Figure 6A:
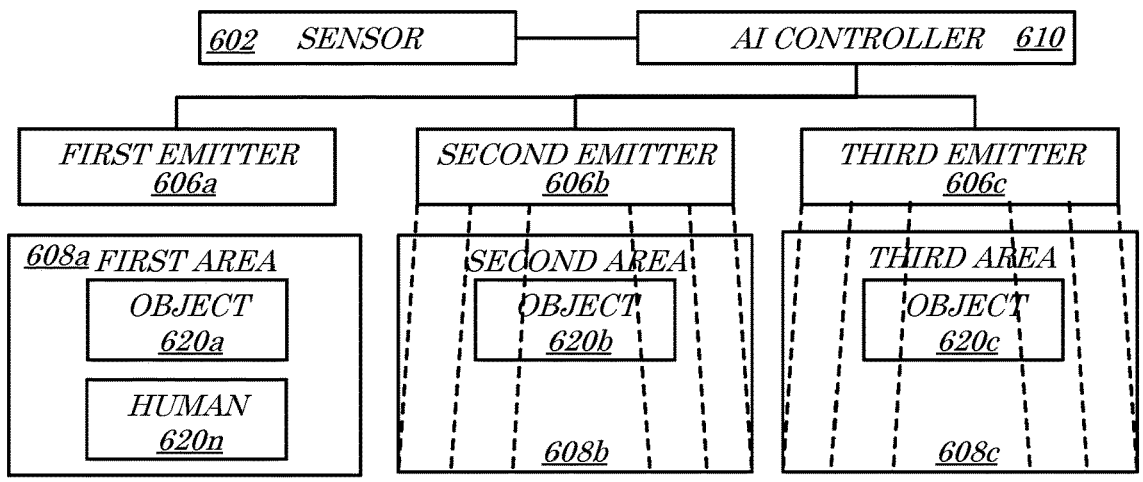
FIG. 6A, FIG. 6B, and FIG. 6C are block diagrams of a safe sterilization system-based method according to some embodiments.
Figure 6B:
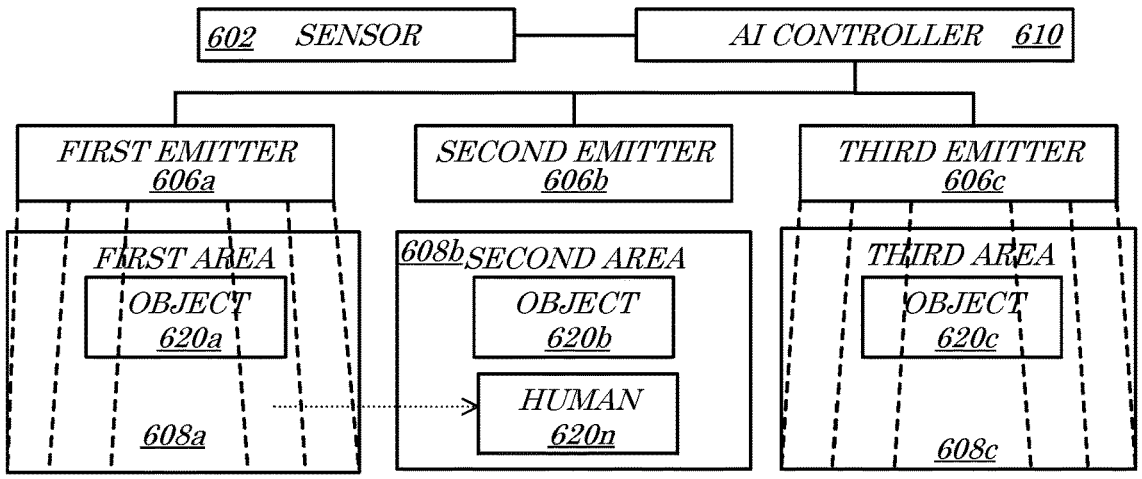
Figure 6C:
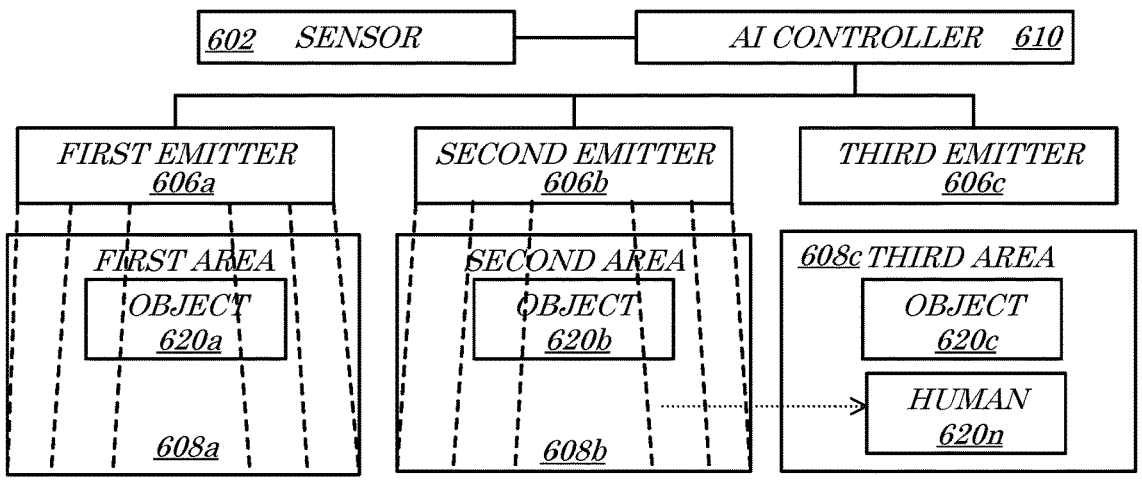

Referring now to FIG. 6A, FIG. 6B, and FIG. 6C, block diagrams of a safe sterilization system-based method 600 according to some embodiments are shown. The safe sterilization system-based method 600 may comprise and/or be effectuated by, for example, a sensor 602 and/or a plurality of sanitizing emitters 606a-c. In some embodiments, the sensor 602 and/or the plurality of sanitizing emitters 606a-c may be disposed (e.g., coupled and/or oriented) to cover one or more of a plurality of areas 608a-c (e.g., sub-areas of a broader location; not separately shown). The sensor 602 may be coupled, for example, to detect and/or acquire data descriptive of each of a first area 608a, a second area 608b, and/or a third area 608c. According to some embodiments, each one of the plurality of sanitizing emitters 606a-c may be oriented to sanitize a respective one of the areas 608a-c. A first emitter 606a may be oriented to sanitize the first area 608a, for example, a second emitter 606b may be oriented to sanitize the second area 608b, and/or a third emitter 606c may be oriented to sanitize the third area 608c. In some embodiments, the sensor 602 and/or the plurality of sanitizing emitters 606a-c may be in communication with an AI controller 610. The AI controller 610 may comprise, for example, an electronic processing device storing, accessing, and/or executing one or more AI programming routines to effectuate embodiments as described herein (e.g., safe and/or autonomous sterilization).

According to some embodiments, various target objects 620a-c may be disposed in the respective areas 608a-c. In an example case of a hospital corridor or room, for example, the first area 608a may comprise a waiting area with a first object 620a comprising a set of chairs or a bench, the second area 608b may comprise an entryway with a second object 620b comprising a set of double doors, and/or the third area 608c may comprise a vending services area with a third object 620c comprising a vending machine. In such embodiments, the first emitter 606a may be selectively activated (e.g., by the AI controller 610) to sanitize the first object 620a, the second emitter 606b may be selectively activated (e.g., by the AI controller 610) to sanitize the second object 620b, and/or the third emitter 606c may be selectively activated (e.g., by the AI controller 610) to sanitize the third object 620c.

In some embodiments, the locations, identifies, and/or classifications of the target objects 620a-c may be known. The AI controller 610 may be programmed with data descriptive of the target objects 620a-c, for example, and/or the AI controller 610 may learn, e.g., by analyzing data from the sensor 602 descriptive of the sub-areas 608a-c over time, the locations, identifies, and/or classifications of the target objects 620a-c. According to some embodiments, the sensor 602 may monitor the areas 608a-c and provide or report readings and/or data to the AI controller 610. In some embodiments, the AI controller 610 may identify, based on data provided by the sensor 602, the presence of a mobile object such as a human 620n. As depicted in FIG. 6A with respect to a first time, for example, the AI controller 610 may identify the human 620n in the first area 608a. According to some embodiments, such as in the case that the AI controller 610 is programmed to avoid sterilizing the human 620n, the AI controller 610 may selectively disable, deactivate, and/or turn off the first emitter 606a, e.g., at the first time. In some embodiments, such as in the case that the sensor 602 is operable to detect the human 620n before entry into the first area 608a, the AI controller 610 may disable the first emitter 606a prior to the human 620n before entry into the first area 608a (e.g., based on an estimated trajectory and/or time of arrival calculated based on data from the sensor 602).

According to some embodiments, and as depicted in FIG. 6B with respect to a second time, the AI controller 610 may identify the human 620n in the second area 608b. In some embodiments, the AI controller 610 may, e.g., in response to the movement of the human 620n, deactivate the second emitter 606b and/or activate the first emitter 606a. Similarly, and as depicted in FIG. 6C with respect to a third time, as the human 620n moves from the second area 608b into the third area 608c, the AI controller 610 may deactivate the third emitter 606c and/or activate (or reactivate) the second emitter 606b. In such a manner, for example, the human 620n (e.g., a pet, service animal, human, etc.) may be free to move about the location (e.g., through any or all of the areas 608a-c) without danger of being exposed to sanitizing activities, while still permitting efficient and/or frequent sanitizing processes (e.g., in an autonomous fashion).

In some embodiments, the plurality of sanitizing emitters 606a-c may comprise any type, quantity, and/or configuration of sanitizing equipment that is or becomes known. One or more of the sanitizing emitters 606a-c may comprise a chemical sprayer, chemical foam or gel dispenser, aerosol diffuser, vaporizer, and/or emitter, and/or sterilizing radiation emitter (e.g., a UV light source). In some embodiments, such as in the case that the location comprises a portion of a hospital, school, and/or other building or structure, one or more of the sanitizing emitters 606a-c may be mounted at one or more advantageous locations within and/or on the building. The first sanitizing emitter 606a may be mounted above the seating are first target object 620a, for example, the second sanitizing emitter 606b may be mounted above the doorway second target object 620b, and/or the third sanitizing emitter 606c may be mounted in front of or within the vending machine third target object 620c. In some embodiments, one or more of the sanitizing emitters 606a-c may be mounted on a mobile device such as a drone, robot, Remote Control (R/C), and/or an autonomous vehicle. In such embodiments, the sanitizing emitters 606a-c may be automatically relocated throughout and/or amongst the areas 608a-c to sanitize the target objects 620a-c and/or to avoid exposing the mobile object 420n to sanitizing substances.

In some embodiments, fewer or more components 602, 606a-c, 608a-c, 610, 620a-n and/or various configurations of the depicted components 602, 606a-c, 608a-c, 610, 620a-n may be included in the safe sterilization system-based method 600 without deviating from the scope of embodiments described herein. In some embodiments, the components 602, 606a-c, 608a-c, 610, 620a-n may be similar in configuration and/or functionality to similarly named and/or numbered components as described herein. In some embodiments, the safe sterilization system-based method 600 (and/or portion and/or component 602, 606a-c, 608a-c, 610, 620a-n thereof) may be utilized in accordance with the method 500 of FIG. 5 herein, and/or portions thereof.

IV. Autonomous Sterilization Apparatus and Articles of Manufacture

Figure 7:
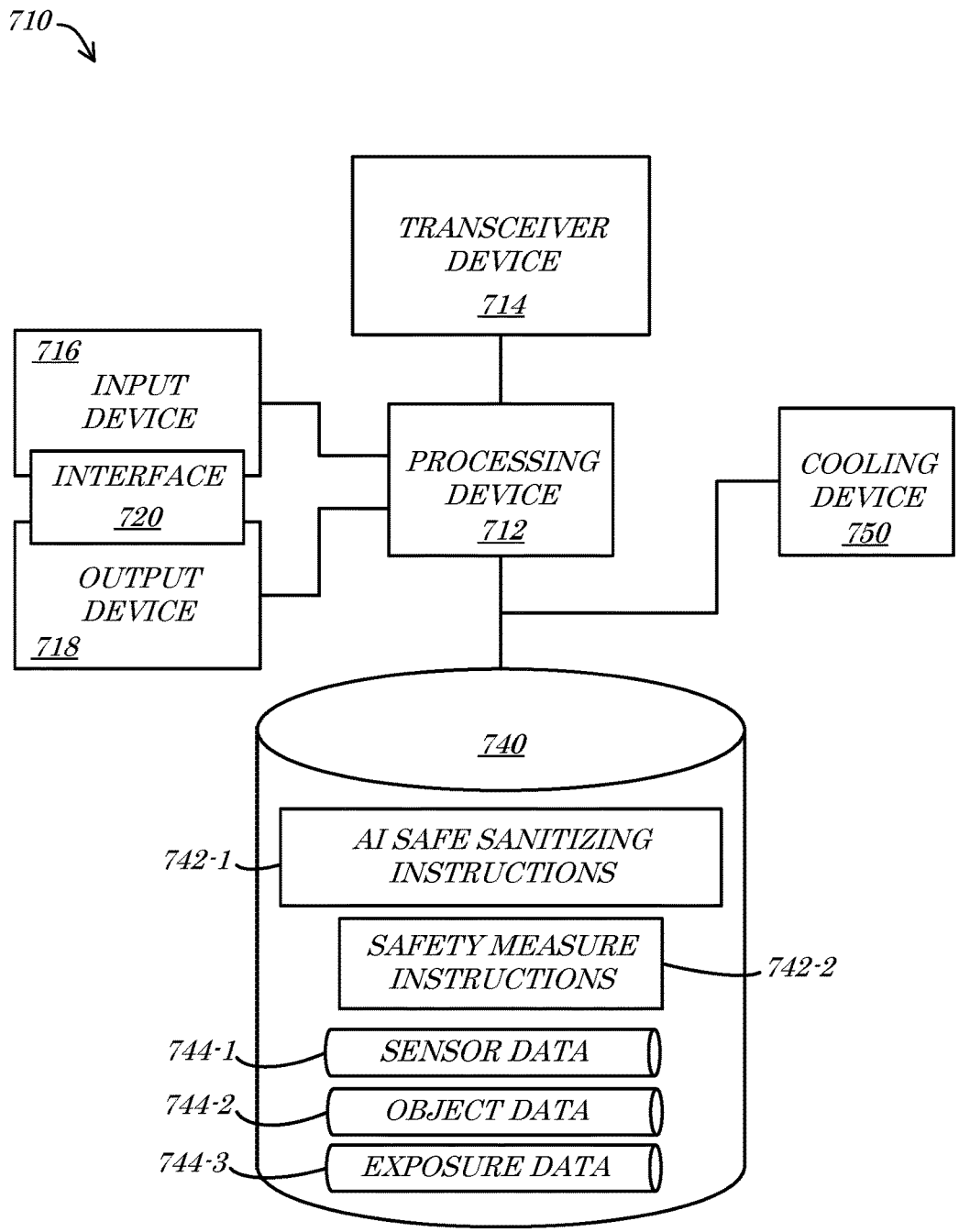
FIG. 7 is a block diagram of an apparatus according to some embodiments.
Figure 8A:
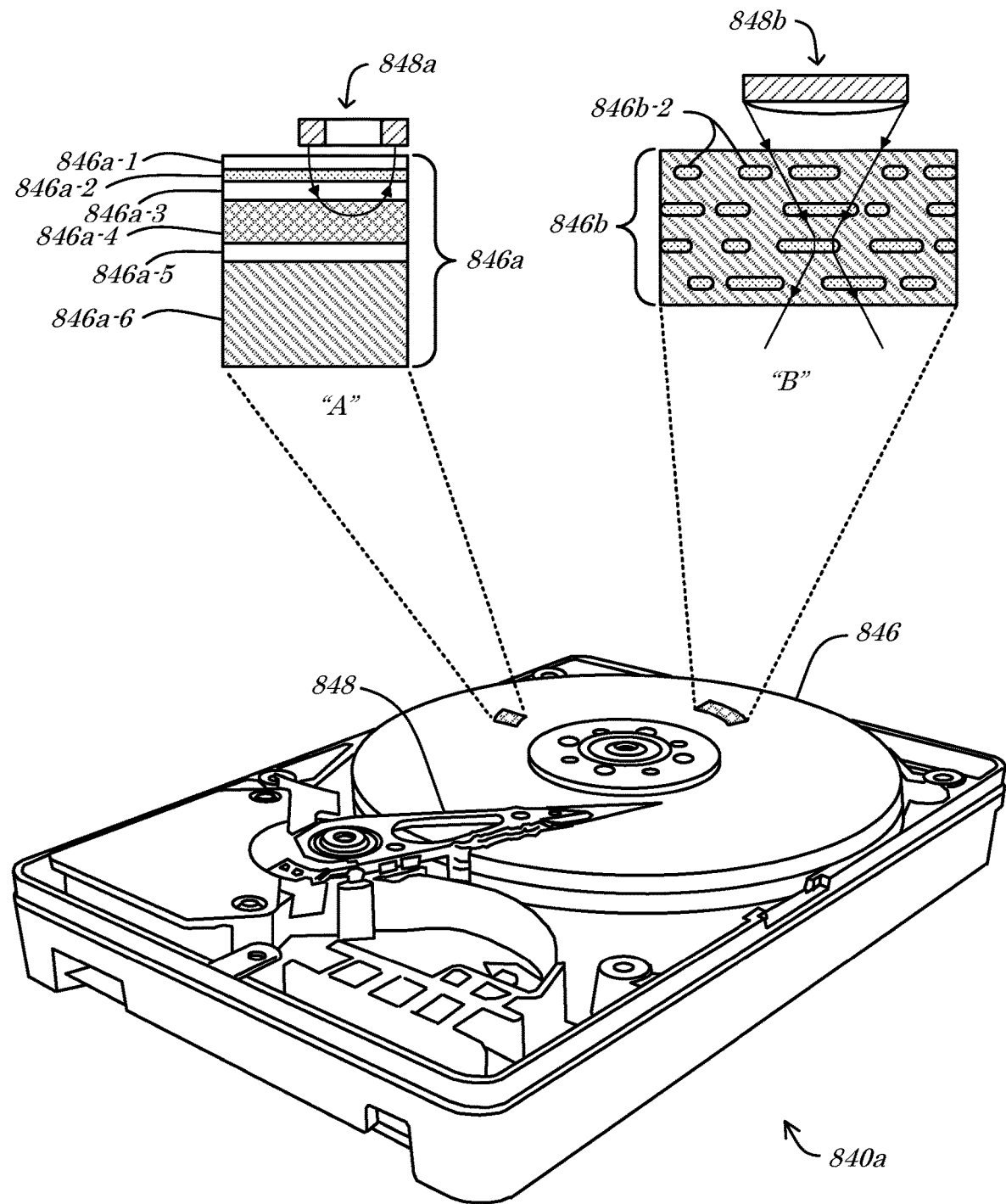
FIG. 8A, FIG. 8B, FIG. 8C, FIG. 8D, and FIG. 8E are perspective diagrams of exemplary data storage devices according to some embodiments.
Figure 8B:
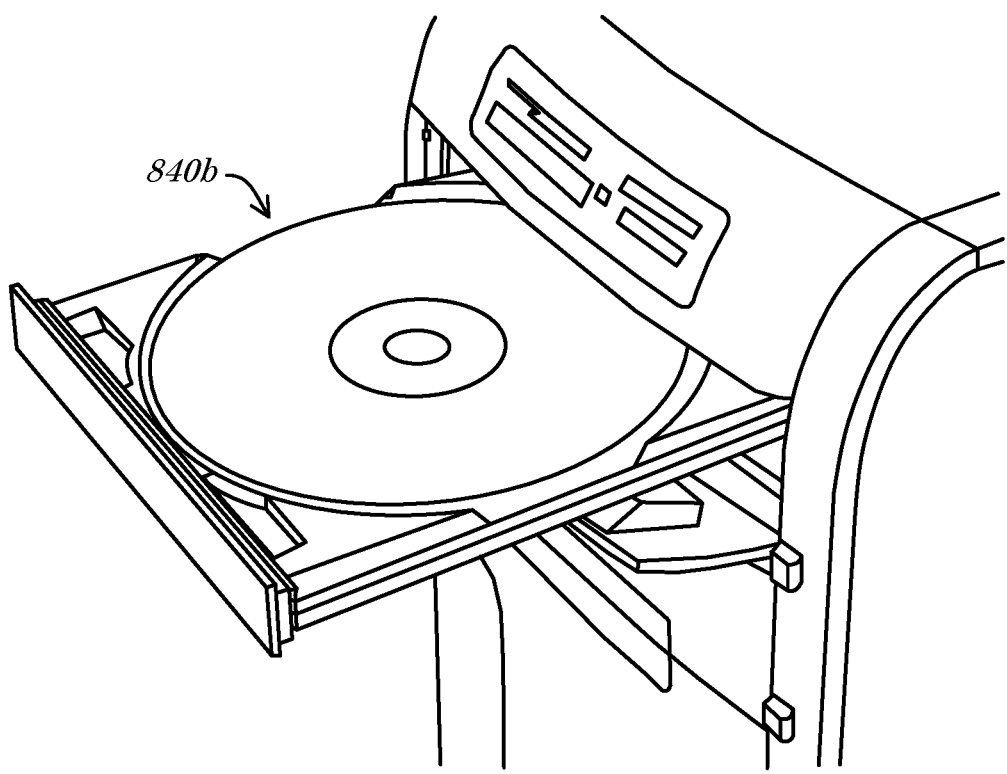
Figure 8C:
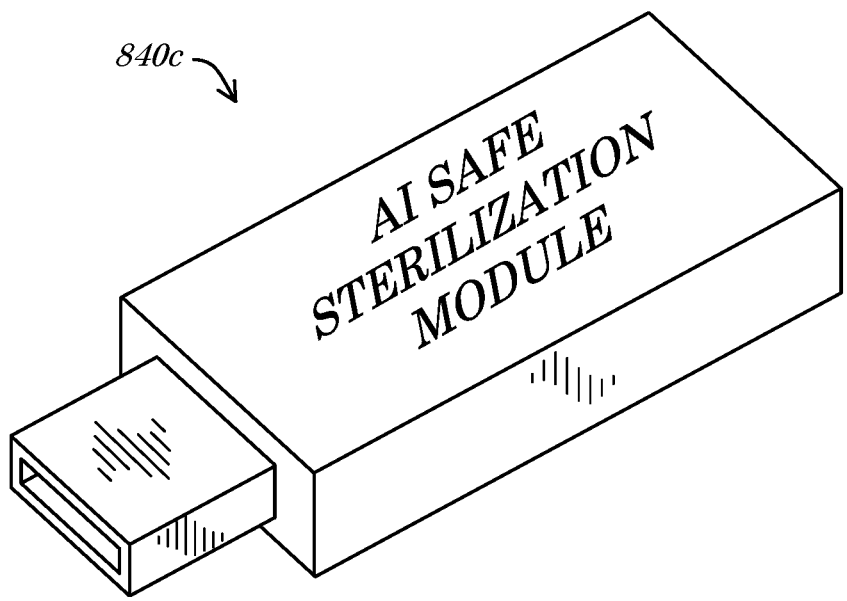
Figure 8D:
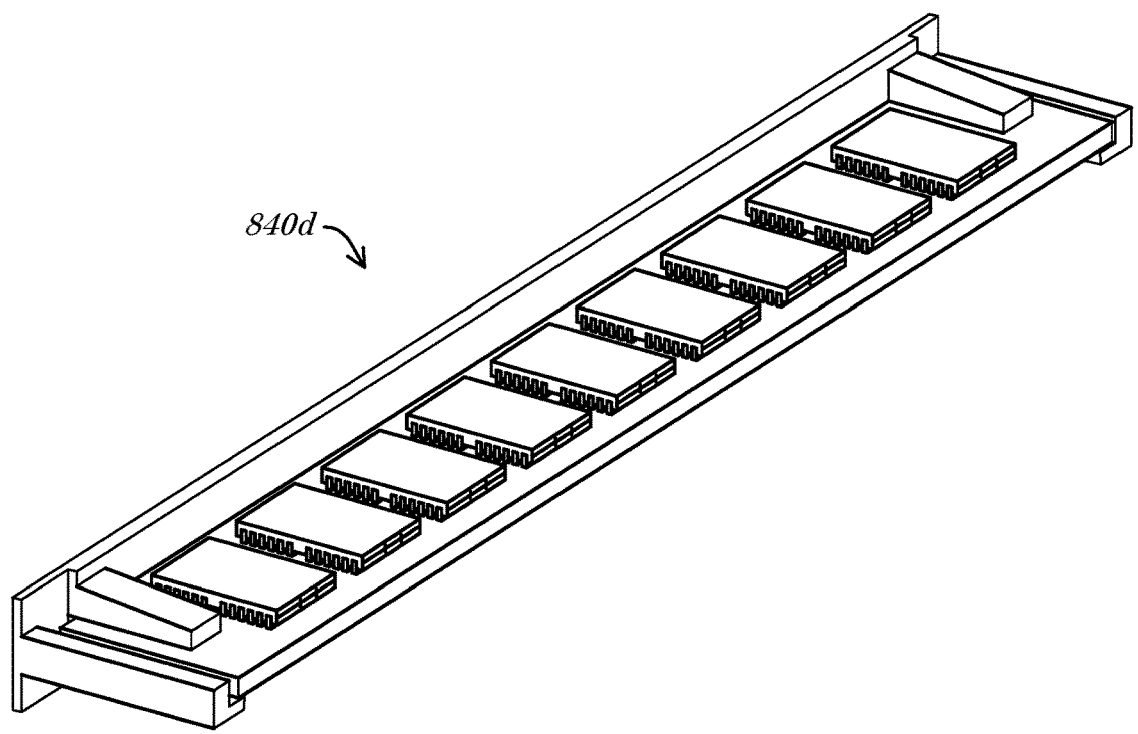
Figure 8E:
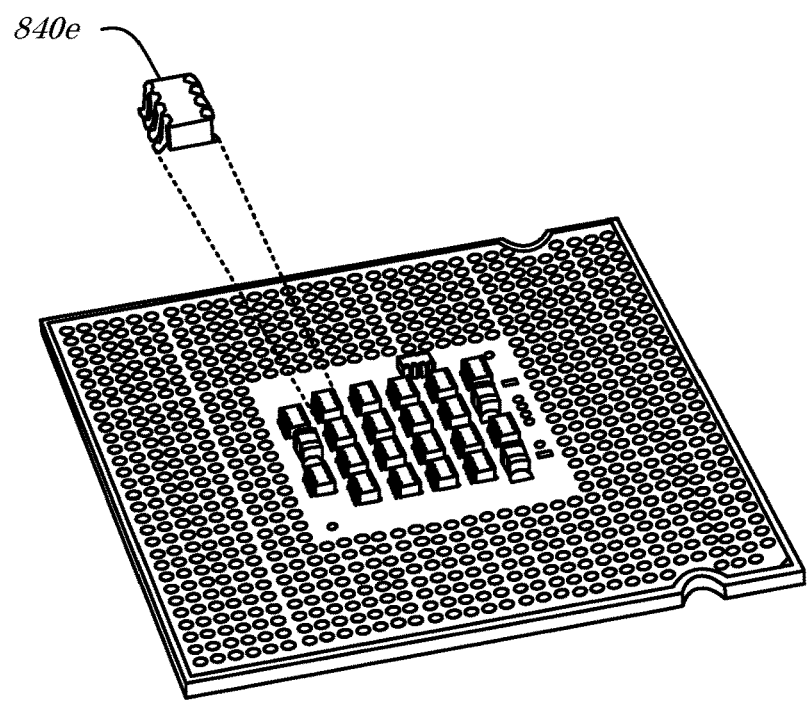

Turning to FIG. 7, a block diagram of an AI device or other apparatus 710 according to some embodiments is shown. In some embodiments, the apparatus 710 may be similar in configuration and/or functionality to any of the controller devices 110, 210, 610, the sensor devices 102, 202a-b, 302a-b, 402, 602, and/or the sanitizing/sterilizing/ emitting devices 106, 206a-b, 306a-6, 406, 606a-c of FIG. 1, FIG. 2, FIG. 3, FIG. 4, and/or FIG. 6 herein. The apparatus 710 may, for example, execute, process, facilitate, and/or otherwise be associated with the methods 500, 600 of FIG. 5 and/or FIG. 6 herein, and/or portions or combinations thereof. In some embodiments, the apparatus 710 may comprise a processing device 712, a transceiver device 714, an input device 716, an output device 718, an interface 720, a memory device 740 (storing various programs and/or instructions 742 and data 744), and/or a cooling device 750. According to some embodiments, any or all of the components 712, 714, 716, 718, 720, 740, 742, 744, 750 of the apparatus 710 may be similar in configuration and/or functionality to any similarly named and/or numbered components described herein. Fewer or more components 712, 714, 716, 718, 720, 740, 742, 744, 750 and/or various configurations of the components 712, 714, 716, 718, 720, 740, 742, 744, 750 be included in the apparatus 710 without deviating from the scope of embodiments described herein.

According to some embodiments, the processor 712 may be or include any type, quantity, and/or configuration of processor that is or becomes known. The processor 612 may comprise, for example, an Intel® IXP 2800 network processor or an Intel® XEON™ Processor coupled with an Intel® E6501 chipset. In some embodiments, the processor 712 may comprise multiple inter-connected processors, microprocessors, and/or micro-engines. According to some embodiments, the processor 712 (and/or the apparatus 710 and/or other components thereof) may be supplied power via a power supply (not shown), such as a battery, an Alternating Current (AC) source, a Direct Current (DC) source, an AC/DC adapter, solar cells, and/or an inertial generator. In the case that the apparatus 710 comprises a server, such as a blade server, necessary power may be supplied via a standard AC outlet, power strip, surge protector, and/or Uninterruptible Power Supply (UPS) device.

In some embodiments, the transceiver device 714 may comprise any type or configuration of communication device that is or becomes known or practicable. The transceiver device 714 may, for example, comprise a Network Interface Card (NIC), a telephonic device, a cellular network device, a router, a hub, a modem, and/or a communications port or cable. According to some embodiments, the transceiver device 714 may also or alternatively be coupled to the processor 712. In some embodiments, the transceiver device 714 may comprise an IR, RF, Bluetooth™, Near-Field Communication (NFC), and/or Wi-Fi® network device coupled to facilitate communications between the processor 712 and another device (not shown).

According to some embodiments, the input device 716 and/or the output device 718 may be communicatively coupled to the processor 712 (e.g., via wired and/or wireless connections and/or pathways) and they may generally comprise any types or configurations of input and output components and/or devices that are or become known, respectively. The input device 716 may comprise, for example, a keyboard that allows an operator of the apparatus 710 to interface with the apparatus 710 and/or may comprise a sensor device and/or array. The output device 718 may, according to some embodiments, comprise a display screen, a sanitizing and/or sterilizing emitter device, and/or other practicable output component and/or device, and/or combination thereof. The output device 718 may, for example, provide an interface via which AI-based safe and/or autonomous sanitizing information is provided to a user (e.g., via a website, display device, speaker, and/or mobile application). According to some embodiments, the input device 716 and/or the output device 718 may comprise and/or be embodied in a single device, such as a touch-screen monitor or display.

The memory device 740 may comprise any appropriate information storage device that is or becomes known or available, including, but not limited to, units and/or combinations of magnetic storage devices (e.g., a hard disk drive), optical storage devices, and/or semiconductor memory devices, such as RAM devices, Read Only Memory (ROM) devices, Single Data Rate Random Access Memory (SDR-RAM), Double Data Rate Random Access Memory (DDR-RAM), and/or Programmable Read Only Memory (PROM). The memory device 740 may, according to some embodiments, store one or more of AI safe sanitizing instructions 742-1, safety measure instructions 742-2, sensor data 744-1, object data 744-2, and/or exposure data 744-3. In some embodiments, the AI safe sanitizing instructions 742-1, safety measure instructions 742-2, sensor data 744-1, object data 744-2, and/or exposure data 744-3 may be utilized by the processor 712 to provide output information via the output device 718 and/or the transceiver device 714.

According to some embodiments, the AI safe sanitizing instructions 742-1 may be operable to cause the processor 712 to process sensor data 744-1, object data 744-2, and/or exposure data 744-3 in accordance with embodiments as described herein. Sensor data 744-1, object data 744-2, and/or exposure data 744-3 received via the input device 716 and/or the transceiver device 718 may, for example, be analyzed, sorted, filtered, decoded, decompressed, ranked, scored, plotted, and/or otherwise processed by the processor 712 in accordance with the AI safe sanitizing instructions 742-1. In some embodiments, sensor data 744-1, object data 744-2, and/or exposure data 744-3 may be fed by the processor 712 through one or more mathematical and/or statistical formulas and/or models in accordance with the AI safe sanitizing instructions 742-1 to automatically identify and/or decide, e.g., based on sensor data, whether to sanitize a location, which sub-portions of the location should be sanitized, and/or what settings should be utilized (e.g., strength, amount, intensity, duration), as described herein.

In some embodiments, the safety measure instructions 742-2 may be operable to cause the processor 712 to process sensor data 744-1, object data 744-2, and/or exposure data 744-3 in accordance with embodiments as described herein. Sensor data 744-1, object data 744-2, and/or exposure data 744-3 received via the input device 716 and/or the transceiver device 718 may, for example, be analyzed, sorted, filtered, decoded, decompressed, ranked, scored, plotted, and/or otherwise processed by the processor 712 in accordance with the safety measure instructions 742-2. In some embodiments, sensor data 744-1, object data 744-2, and/or exposure data 744-3 may be fed by the processor 712 through one or more mathematical and/or statistical formulas and/or models in accordance with the safety measure instructions 742-2 to automatically implement one or more safety measures to protect living objects at a location and/or to reduce damage to non-living objects, such as by preventing, pausing, and/or delaying sterilization procedures, steering and/or masking sterilization output and/or substances away from certain areas and/or objects, and/or adjusting sanitizing settings to reduce and/or manage exposure of objects to sanitizing output and/or substances (e.g., to be maintained within acceptable thresholds and/or guidelines), as described herein.

According to some embodiments, the apparatus 710 may comprise the cooling device 750. According to some embodiments, the cooling device 750 may be coupled (physically, thermally, and/or electrically) to the processor 712 and/or to the memory device 740. The cooling device 750 may, for example, comprise a fan, heat sink, heat pipe, radiator, cold plate, and/or other cooling component or device or combinations thereof, configured to remove heat from portions or components of the apparatus 710.

Any or all of the exemplary instructions and data types described herein and other practicable types of data may be stored in any number, type, and/or configuration of memory devices that is or becomes known. The memory device 740 may, for example, comprise one or more data tables or files, databases, table spaces, registers, and/or other storage structures. In some embodiments, multiple databases and/or storage structures (and/or multiple memory devices 740) may be utilized to store information associated with the apparatus 710. According to some embodiments, the memory device 740 may be incorporated into and/or otherwise coupled to the apparatus 710 (e.g., as shown) or may simply be accessible to the apparatus 710 (e.g., externally located and/or situated).

Referring now to FIG. 8A, FIG. 8B, FIG. 8C, FIG. 8D, and FIG. 8E, perspective diagrams of exemplary data storage devices 840a-e according to some embodiments are shown. The data storage devices 840a-e may, for example, be utilized to store instructions and/or data, such as the AI safe sanitizing instructions 742-1, safety measure instructions 742-2, sensor data 744-1, object data 744-2, and/or exposure data 744-3, each of which is presented in reference to FIG. 7 herein. In some embodiments, instructions stored on the data storage devices 840a-e may, when executed by a processor, cause the implementation of and/or facilitate the methods 500, 600 of FIG. 5 and/or FIG. 6 herein, and/or portions or combinations thereof.

According to some embodiments, the first data storage device 840a may comprise one or more various types of internal and/or external hard drives. The first data storage device 840a may, for example, comprise a data storage medium 846 that is read, interrogated, and/or otherwise communicatively coupled to and/or via a disk reading device 848. In some embodiments, the first data storage device 840a and/or the data storage medium 846 may be configured to store information utilizing one or more magnetic, inductive, and/or optical means (e.g., magnetic, inductive, and/or optical-encoding). The data storage medium 846, depicted as a first data storage medium 846a for example (e.g., breakout cross-section "A"), may comprise one or more of a polymer layer 846a-1, a magnetic data storage layer 846a-2, a non-magnetic layer 846a-3, a magnetic base layer 846a-4, a contact layer 846a-5, and/or a substrate layer 846a-6. According to some embodiments, a magnetic read head 848a may be coupled and/or disposed to read data from the magnetic data storage layer 846a-2.

In some embodiments, the data storage medium 846, depicted as a second data storage medium 846b for example (e.g., breakout cross-section "B"), may comprise a plurality of data points 846b-2 disposed with the second data storage medium 846b. The data points 846b-2 may, in some embodiments, be read and/or otherwise interfaced with via a laser-enabled read head 848b disposed and/or coupled to direct a laser beam through the second data storage medium 846b.

In some embodiments, the second data storage device 840b may comprise a CD, CD-ROM, DVD, Blu-Ray™ Disc, and/or other type of optically-encoded disk and/or other storage medium that is or becomes know or practicable. In some embodiments, the third data storage device 840c may comprise a USB keyfob, dongle, and/or other type of flash memory data storage device that is or becomes know or practicable. In some embodiments, the fourth data storage device 840d may comprise RAM of any type, quantity, and/or configuration that is or becomes practicable and/or desirable. In some embodiments, the fourth data storage device 840d may comprise an off-chip cache, such as a Level 2 (L2) cache memory device. According to some embodiments, the fifth data storage device 840e may comprise an on-chip memory device, such as a Level 1 (L1) cache memory device.

The data storage devices 840a-e may generally store program instructions, code, and/or modules that, when executed by a processing device cause a particular machine to function in accordance with one or more embodiments described herein. The data storage devices 840a-e depicted in FIG. 8A, FIG. 8B, FIG. 8C, FIG. 8D, and FIG. 8E are representative of a class and/or subset of computer-readable media that are defined herein as "computer-readable memory" (e.g., non-transitory memory devices as opposed to transmission devices or media).

V. Rules of Interpretation

Throughout the description herein and unless otherwise specified, the following terms may include and/or encompass the example meanings provided. These terms and illustrative example meanings are provided to clarify the language selected to describe embodiments both in the specification and in the appended claims, and accordingly, are not intended to be generally limiting. While not generally limiting and while not limiting for all described embodiments, in some embodiments, the terms are specifically limited to the example definitions and/or examples provided. Other terms are defined throughout the present description.

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

Devices that are in communication with each other need not be in continuous communication with each other, unless expressly specified otherwise.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

It will be understood that various modifications can be made to the embodiments of the present disclosure herein without departing from the scope thereof. Therefore, the above description should not be construed as limiting the disclosure, but merely as embodiments thereof. Those skilled in the art will envision other modifications within the scope of the invention as defined by the claims appended hereto.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As utilized herein, the term "safe", e.g., as utilized in the context of sanitizing operations, generally refers to any process, method, and/or procedure that limits exposure of living objects to sanitizing substances such as chemicals and/or radiation. Depending upon the type of substance and/or the type of living object (e.g., human, dog, cat, etc.), different acceptable levels of exposure may be known and/or updated from time to time by various third-parties such as health organizations, universities, medical groups, etc.

As utilized herein, the terms "sanitizing", "sterilizing", "disinfecting", and "cleaning" may generally be utilized interchangeably and may generally refer to any process, method, procedure, and/or act that attempts to and/or results in a removal, destruction, and/or disabling of one or more potentially harmful substances, contaminants, and/or pollutants. In some embodiments, sanitizing may comprise a species of cleaning and/or disinfecting and may refer to a statistically significant reduction of microorganisms (e.g., in a treatment area). According to some embodiments, sterilizing may comprise a species of cleaning and/or disinfecting (and/or of sanitizing) and may refer to a complete destruction and/or deactivation of microorganisms (e.g., in a treatment area).

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. An autonomous sanitizing system, comprising:
   an electronic processing device;
   an electronic sensor device in communication with the electronic processing device;
   an electronically actuated sanitizing device in communication with the electronic processing device; and
   a non-transitory memory device storing (i) coded logic and (ii) operating instructions that when executed by the electronic processing device, result in:
   acquiring, by the electronic sensor device, data descriptive of a location;
   identifying, by the electronic processing device, a sanitizing process trigger;

computing, by an execution of the coded logic by the electronic processing device, and based on an evaluation of the sanitizing process trigger, a determination that an autonomous sanitizing process should be initiated;

identifying, by the electronic processing device, a sanitizing process exception rule;

computing, by an execution of the coded logic by the electronic processing device, and based on an evaluation of the sanitizing process exception rule, a determination that an exception exists;

identifying, by the electronic processing device and based on the determination that the exception exists, a safety measure; and actuating, by the electronic processing device, the safety measure.

2. The autonomous sanitizing system of claim 1, wherein the safety measure comprises:

identifying, by the electronic processing device and based on the data descriptive of the location, a sub-area to be sanitized;

activating the electronically actuated sanitizing device; and sanitizing, by the electronically actuated sanitizing device and in response to the activating, the identified sub-area.

3. The autonomous sanitizing system of claim 2, wherein the sanitizing of the sub-area by the electronically actuated sanitizing device is conducted by selectively directing a sanitizing substance to the sub-area.

4. The autonomous sanitizing system of claim 2, wherein the sanitizing of the sub-area by the electronically actuated sanitizing device is conducted by masking an emission of a sanitizing substance such that it is limited to being emitted to the sub-area.

5. The autonomous sanitizing system of claim 4, wherein the sanitizing substance comprises UV light and wherein the masking comprises selectively activating at least one portion of an LCD display through which the UV light is directed.

6. The autonomous sanitizing system of claim 2, wherein the electronically actuated sanitizing device comprises a sanitizing substance emitter and wherein the sanitizing comprises emitting, by the electronically actuated sanitizing device, at least one of a chemical and UV light.

7. The autonomous sanitizing system of claim 1, wherein the electronic sensor device comprises at least one of a LiDAR device, a radar device, a PIR device, an acoustic ranging device, a pressure sensor, and a temperature sensor.

8. The autonomous sanitizing system of claim 1, wherein the safety measure comprises delaying initiation of an autonomous sanitizing process.

9. The autonomous sanitizing system of claim 1, wherein the safety measure comprises reducing at least one of a sanitizing substance strength and a duration of an autonomous sanitizing process.

10. The autonomous sanitizing system of claim 1, wherein the computing of the determination that the exception exists comprises:

analyzing the data descriptive of the location; and identifying, based on the analyzing, a living object at the location.

11. A method of autonomous and safe sterilization of a location, comprising:

acquiring, by an electronic sensor device, data descriptive of a location;

identifying, by an electronic processing device in communication with the electronic sensor device, a sanitizing process trigger;

computing, by an execution of coded logic by the electronic processing device, and based on an evaluation of the sanitizing process trigger, a determination that an autonomous sanitizing process should be initiated;

identifying, by the electronic processing device, a sanitizing process exception rule;

computing, by the execution of the coded logic by the electronic processing device, and based on an evaluation of the sanitizing process exception rule with respect to the data descriptive of the location, a determination that an exception exists;

identifying, by the electronic processing device and based on the determination that the exception exists, a safety measure;

actuating, by the electronic processing device, the safety measure; and sterilizing, by a sterilization device in communication with the electronic processing device, at least one portion of the location.

12. The method of claim 11, further comprising:

identifying, by the electronic processing device and based on the determination that the exception exists, the at least one portion of the location to sanitize.

13. The method of claim 11, wherein the at least one portion of the location comprises a sub-area of the location, further comprising:

receiving, by a location device in communication with the sterilization device, a sterilizing substance; and limiting, by the location device, emission of the sterilizing substance to the at least one portion of the location.

14. The method of claim 11, wherein the location comprises an interior of an autonomous vehicle.

15. The method of claim 11 further comprising:

outputting, during the sterilizing and via an output device, a notification of the sterilizing.

16. The method of claim 11, wherein the actuating of the safety measure comprises:

at least one of closing and locking at least one door of an autonomous vehicle.

17. The method of claim 11, wherein the sterilization device comprises a sterilizing substance emitter and wherein the sterilizing comprises emitting, by the sterilization device, at least one of a chemical and UV light.

18. The method of claim 11, wherein the electronic sensor device comprises at least one of a LiDAR device, a radar device, a PIR device, an acoustic ranging device, a pressure sensor, and a temperature sensor.

19. A method of autonomous and safe sterilization of a location, comprising:

acquiring, at a first time and by an electronic sensor device, data descriptive of a first position of a human at a location;

identifying, by an electronic processing device in communication with the electronic sensor device, a sanitizing process trigger;

computing, by an execution of coded logic by the electronic processing device, and based on an evaluation of the sanitizing process trigger, a determination that an autonomous sanitizing process should be initiated;

actuating, by the electronic processing device and based on the first location of the human at the location, a first subset of sanitizing devices at the location;

acquiring, at a second time and by the electronic sensor device, data descriptive of a second position of the human at the location; and actuating, by the electronic processing device and based on the second location of the human at the location, a second subset of sanitizing devices at the location.

20. The method of claim 19, wherein the first subset of sanitizing devices at the location comprises at least one sanitizing device disposed to sanitize the second location and wherein the second subset of sanitizing devices at the location comprises at least one sanitizing device disposed to sanitize the first location.

\* \* \* \* \*